(12) United States Patent
Tsai et al.

(10) Patent No.: US 11,293,067 B2
(45) Date of Patent: Apr. 5, 2022

(54) METHOD FOR GENOTYPING MYCOBACTERIUM TUBERCULOSIS

(71) Applicant: NATIONAL HEALTH RESEARCH INSTITUTES, Miaoli County (TW)

(72) Inventors: Shih-Feng Tsai, Miaoli County (TW); Chien-Hsing Lin, Miaoli County (TW); Horng-Yunn Dou, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 520 days.

(21) Appl. No.: 15/921,323

(22) Filed: Mar. 14, 2018

(65) Prior Publication Data

US 2018/0208974 A1   Jul. 26, 2018

Related U.S. Application Data

(63) Continuation of application No. 14/089,990, filed on Nov. 26, 2013, now abandoned.

(60) Provisional application No. 61/730,033, filed on Nov. 26, 2012.

(51) Int. Cl.
*C12Q 1/689*   (2018.01)

(52) U.S. Cl.
CPC ....... *C12Q 1/689* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 6,294,328 B1 | 9/2001 | Fleischmann et al. | |
| 2009/0285847 A1 | 11/2009 | Felgner et al. | |
| 2011/0105531 A1* | 5/2011 | Massire | A61P 31/06 514/255.06 |

OTHER PUBLICATIONS

Lowe et al., "A computer program for selection of oligonucleotide primers chain reactions," Nucleic Acids research, vol. 18(7), 1990, pp. 1757-1761.
International Search Report and Written Opinion, PCT/US2013/071819, dated May 23, 2014, 12 pages.
Genbank, NCBI Reference Sequencde: NC_000962.2 "*Mycobacterium tuberculosis* H37Rv chromosome, complete genome," [online], dated Aug. 20, 2012.
Brudey, K., et al., "*Mycobacterium tuberculosis* complex genetic diversity: mining the fourth international spoligotyping database (SpolDB4) for classification, population genetics and epidemiology," BMC Microbiology, (2006), vol. 6, No. 23, 17 pages.
Van Deutekom, H., et al., "Molecular Typing of *Mycobacterium tuberculosis* by Mycobacterial Interspersed Repetitive Unit-Variable-Number Tandem Repeat Analysis, a More Accurate Method for Identifying Epidemiological Links between Patients with Tuberculosis," Journal of Clinical Microbiology, (Sep. 2005), vol. 43, No. 9, pp. 4473-4479.
Supply, P., et al., "Variable human minisatellite-like regions in the *Mycobacterium tuberculosis* genome," Molecular Microbiology (2000) vol. 36, No. 3, p. 762-771.
Comas, I., et al., "Genotyping of Genetically Monomorphic Bacteria: DNA Sequencing in *Mycobacterium tuberculosis* Highlights the Limitations of Current Methodologies," PLOS One, (Nov. 12, 2009), 11 pages.
Mazars, E., et al., "High-resolution minisatellite-based typing as a portable approach to global analysis of *Mycobacterium tuberculosis* molecular epidemiology," PNAS, (Feb. 13, 2001), vol. 98, No. 4, pp. 1901-1906.
Dou, H-Y, et al., "Utility and evaluation of new variable-Number tandem-repeat systems for genotyping *Mycobacterial tuberculosis* isolates," Journal of Microbiological Methods, (2009), vol. 77, pp. 127-129.
Dou, H-Y, et al., "Molecular epidemiology and evolutionary genetics of *Mycobacterium tuberculosis* in Taipei," BMC Infectious Diseases, (2008), vol. 8, No. 170, 12 pages.
Chang, J-R., et al., "Genotypic analysis of genes associated with transmission and drug resistance in the Beijing lineage of *Mycobacterium tuberculosis*," Clin. Microbiol. Infec. (2011), vol. 17, pp. 1391-1396.
Dou, H-Y., et al., "Associations of *Mycobacterium tuberculosis* genotypes with different ethnic and migratory populations in Taiwan," Infection, Genetics and Evolution, vol. 8, (2008), pp. 323-330.
Margulies, M., et al., "Genome sequencing in microfabricated high-density picolitre reactors," Nature, vol. 437, (Sep. 25, 2005), 6 pages.
Bouakaze, C., et al., "Matrix-Assisted Laser Desorption Ionization-Time of Flight Mass Spectrometry-Based Single Nucleotide Polymorphism Genotyping Assay Using iPLEX Gold Technology for Identification of *Mycobacterium tuberculosis* Complex Species and Lineages," Journal of Clinical Microbiology, (Sep. 2011), vol. 49, No. 9, pp. 3292-3299.
Invitation to Pay Additional Fees, PCT/US2013/071819, dated Mar. 19, 2014, 2 pages.

\* cited by examiner

*Primary Examiner* — Samuel C Woolwine
*Assistant Examiner* — Carolyn L Greene
(74) *Attorney, Agent, or Firm* — Muncy, Geissler, Olds & Lowe, P.C.

(57) ABSTRACT

The present application provides a method for genotyping *M. tuberculosis*, comprising obtaining amplifying and obtaining a first DNA fragment from a DNA sample by using one or more primer sets selected from the group consisting of primer sets 1 to 25 (SEQ ID Nos. 1 to 50); amplifying and obtaining a second DNA fragment from the obtained first DNA fragment by using one or more extension primers selected from the group consisting of SEQ ID Nos. 51 to 75; and detecting the second DNA fragment by using mass spectrometry, particularly by matrix-assisted laser desorption ionization time-of-flight mass spectrometry (MALDI-TOF MS).

6 Claims, 14 Drawing Sheets

Specification includes a Sequence Listing.

(A)

(B)

| Multiplex Well ID | varID | H37Rv genome position (NC_000962.2) | reference allele | variant allele | PCR Forward Primer | PCR Reverse Primer | Extension Primer |
|---|---|---|---|---|---|---|---|
| W1 | 94 | 128290 | G | T | SEQ ID No. 1 | SEQ ID No. 2 | SEQ ID No. 51 |
| W1 | 247 | 375095 | C | G | SEQ ID No. 3 | SEQ ID No. 4 | SEQ ID No. 52 |
| W1 | 270 | 430332 | A | G | SEQ ID No. 5 | SEQ ID No. 6 | SEQ ID No. 53 |
| W1 | 450 | 756840 | T | C | SEQ ID No. 7 | SEQ ID No. 8 | SEQ ID No. 54 |
| W1 | 503 | 848652 | A | G | SEQ ID No. 9 | SEQ ID No. 10 | SEQ ID No. 55 |
| W1 | 570 | 991896 | T | C | SEQ ID No. 11 | SEQ ID No. 12 | SEQ ID No. 56 |
| W1 | 573 | 996219 | G | A | SEQ ID No. 13 | SEQ ID No. 14 | SEQ ID No. 57 |
| W1 | 998 | 1810066 | G | A | SEQ ID No. 15 | SEQ ID No. 16 | SEQ ID No. 58 |
| W1 | 1182 | 2165554 | A | G | SEQ ID No. 17 | SEQ ID No. 18 | SEQ ID No. 59 |
| W1 | 1626 | 3078579 | G | A | SEQ ID No. 19 | SEQ ID No. 20 | SEQ ID No. 60 |
| W1 | 1943 | 3734189 | A | T | SEQ ID No. 21 | SEQ ID No. 22 | SEQ ID No. 61 |
| W1 | 2236 | 4221423 | C | T | SEQ ID No. 23 | SEQ ID No. 24 | SEQ ID No. 62 |

Figure 10

| Multiplex Well ID | varID | H37Rv genome position (NC_000962.2) | reference allele | variant allele | PCR Forward Primer | PCR Reverse Primer | Extension Primer |
|---|---|---|---|---|---|---|---|
| W2 | 128 | 178812 | G | A | SEQ ID No. 25 | SEQ ID No. 26 | SEQ ID No. 63 |
| W2 | 164 | 243118 | G | A | SEQ ID No. 27 | SEQ ID No. 28 | SEQ ID No. 64 |
| W2 | 732 | 1300047 | G | A | SEQ ID No. 29 | SEQ ID No. 30 | SEQ ID No. 65 |
| W2 | 1060 | 1932201 | A | G | SEQ ID No. 31 | SEQ ID No. 32 | SEQ ID No. 66 |
| W2 | 1181 | 2165256 | T | G | SEQ ID No. 33 | SEQ ID No. 34 | SEQ ID No. 67 |
| W2 | 1673 | 3157993 | A | C | SEQ ID No. 35 | SEQ ID No. 36 | SEQ ID No. 68 |
| W2 | 1799 | 3426415 | T | C | SEQ ID No. 37 | SEQ ID No. 38 | SEQ ID No. 69 |
| W2 | 2000 | 3797876 | C | T | SEQ ID No. 39 | SEQ ID No. 40 | SEQ ID No. 70 |
| W2 | 2137 | 4061113 | G | T | SEQ ID No. 41 | SEQ ID No. 42 | SEQ ID No. 71 |
| W2 | 2329 | 4352162 | A | C | SEQ ID No. 43 | SEQ ID No. 44 | SEQ ID No. 72 |
| W3 | 246 | 374353 | A | G | SEQ ID No. 45 | SEQ ID No. 46 | SEQ ID No. 73 |
| W3 | 1093 | 2008738 | G | A | SEQ ID No. 47 | SEQ ID No. 48 | SEQ ID No. 74 |
| W3 | 2035 | 3859376 | C | T | SEQ ID No. 49 | SEQ ID No. 50 | SEQ ID No. 75 |

Figure 10 (cont.)

| Method | This invention | Prior art | | |
|---|---|---|---|---|
| | tagSNP typing | IS6110 genotyping | Spoligotyping | MIRU typing |
| Target | 25 tagSNPs | Insertion sequence 6110 marker | 1 repeat locus | 12 MIRU loci |
| Method | MALDI-TOF Mass Array | Restriction-fragment length polymorphism analysis | Probe hybridization | Gel electrophoresis |
| Test Time | 1-2 day | 2-3 day | 1-2 day | 1-2 day |
| Sensitivity | High | Medium | Very low | Medium |
| Through-put | 192 | 16 | 40 | 16 |
| Sputum sample | Yes | No (>6 weeks to get DNA sample) | No (>6 weeks to get DNA sample) | No (>6 weeks to get DNA sample) |

Figure 11

METHOD FOR GENOTYPING *MYCOBACTERIUM TUBERCULOSIS*

CROSS-REFERENCE TO RELATED APPLICATIONS

This application is a continuation of co-pending U.S. application Ser. No. 14/089,990, filed on Nov. 26, 2013, for which priority is claimed under 35 U.S.C. § 120; and this application claims priority of U.S. Provisional Application No. 61/730,033 filed on Nov. 26, 2012 under 35 U.S.C. § 119(e), the entire contents of all of which are hereby incorporated by reference.

INCORPORATION-BY-REFERENCE OF THE SEQUENCE LISTING

This application includes an electronically submitted sequence listing in .txt format. The .txt file contains a sequence listing entitled "2018-03-14-Sequence-Listing" created on Mar. 14, 2018 and is 44,366 bytes in size. The sequence listing contained in this .txt file is part of the specification and is hereby incorporated by reference herein in its entirety.

BACKGROUND OF THE INVENTION

1. Field of the Invention

The present invention relates to the method for detecting *Mycobacterium tuberculosis*, and more particularly for genotyping *M. tuberculosis*.

2. Description of the Related Art

*Tuberculosis* (TB) is a worldwide healthcare concern. It has been characterized by the World Health Organization (WHO) as an epidemic and estimated that one-third of the world's population has been infected with *Mycobacterium tuberculosis* (MTB). Epidemiologic studies have revealed that various genotypes of *M. tuberculosis* (MTB) may be prevalent in different geographic regions and that genotype distribution is associated with population migrations. Whether MTB genomic diversity influences human disease in clinical settings remains an open question.

The complete genome of H37Rv strain MTB was published in 1988, which has a length of about 4 Mb and contains about 4000 genes. MTB can be classified as six major strains and 15 subordinate strains. Genomic variations affect the transmission, virulence, antimicrobial resistance and other attributes of the MTB, so that the development of molecular techniques for differentiating various MTB isolates is of considerable interest in epidemiological studies.

Genotyping methods aiming at generating phylogenetically informative data have been developed to investigate multiple clinical samples from different sources. Currently, there are two genotyping methods that are commonly used to study *tuberculosis* transmission (van Deutekom H. et al., *J Clin Microbiol* 2005, 43(9):4473-4479). Spoligotyping is based on polymorphisms in the direct repeat (DR) locus, which is consisted of 36-bp DR copies interspaced by non-repetitive spacer sequence. It is a PCR-based reverse hybridization technique for MTB genotyping. The portable data format facilities easy inter-laboratory comparison. To date published, freely accessible databases for strain lineage identification have been developed on the basis of spoligotype signature matching (Brudey K et al., *BMC Microbiol* 2006, 6:23). Another molecular technique for strain typing of MTB is based on variable number tandem repeats (VNTRs) of mycobacterial interspersed repetitive units (MIRUs) (Mazars E. et al., *Proc Natl Acad Sci USA* 2001, 98(4):1901-1906; Comas I. et al., *PLoS One* 2009, 4(11): e7815; Supply P. et al., *Mol Microbiol* 2000, 36(3):762-771). This method is based on the number of repeats observed at each of the 12, 15 or 24 selected MIRU loci, determined using a PCR-based method.

However, the conventional methods for genotyping MTB have disadvantages including the requirement of large amount of DN sample, time-consumption, insufficient sensitivity and specificity, inability for genotyping particular strains. Therefore, there is a need for the improved method for genotyping MTB.

SUMMARY

The present application describes a primer set for genotyping *M. tuberculosis* selected from one of the group consisting of primer sets 1-25.

The present application provides an extension primer for genotyping *M. tuberculosis* selected from one of the group consisting of SEQ ID Nos. 51-75.

The present application provides a combination of single-nucleotide polymorphism markers of *M. tuberculosis* selected from the group consisting of "T" at position 301 of SEQ ID No. 76, "A" at position 301 of SEQ ID No. 77, "A" at position 301 of SEQ ID No. 78, "G" at position 301 of SEQ ID No. 79, "G" at position 301 of SEQ ID No. 80, "G" at position 301 of SEQ ID No. 81, "C" at position 301 of SEQ ID No. 82, "G" at position 301 of SEQ ID No. 83, "C" at position 301 of SEQ ID No. 84, "A" at position 301 of SEQ ID No. 85, "A" at position 301 of SEQ ID No. 86, "A" at position 301 of SEQ ID No. 87, "G" at position 301 of SEQ ID No. 88, "A" at position 301 of SEQ ID No. 89, "G" at position 301 of SEQ ID No. 90, "G" at position 301 of SEQ ID No. 91, "A" at position 301 of SEQ ID No. 92, "C" at position 301 of SEQ ID No. 93, "C" at position 301 of SEQ ID No. 94, "T" at position 301 of SEQ ID No. 95, "T" at position 301 of SEQ ID No. 96, "T" at position 301 of SEQ ID No. 97, "T" at position 301 of SEQ ID No. 98, "T" at position 301 of SEQ ID No. 99, and "C" at position 301 of SEQ ID No. 100.

The present application also provides a method for genotyping *M. tuberculosis* comprising obtaining a sample, amplifying and obtain at least one of first DNA fragment by using one or more primer sets selected from the group consisting of primer sets 1 to 25 (SEQ ID Nos. 1 to 50), amplifying and obtain at least one of second DNA fragment by using the obtained first DNA fragment as template and using one or more extension primers selected from the group consisting of SEQ ID Nos. 51 to 75, and detecting the second DNA fragment by using mass spectrometry.

In other embodiments, the present application also provides a kit for genotyping *M. tuberculosis* comprising at least one primer set selected from the group consisting of primer sets 1 to 25 (SEQ ID Nos. 1 to 50), and at least one extension primer selected from the group consisting of SEQ ID Nos. 51 to 75.

BRIEF DESCRIPTION OF THE DRAWINGS

FIG. 10 shows the PCR primers, the extension primers, the positions and the correspondent alleles for the 25 tag-SNPs with the multiplex reaction well scheme.

FIG. 11 shows the comparisons of the present application and the conventional genotyping methods.

DETAILED DESCRIPTION OF THE EMBODIMENTS

Figure 1:
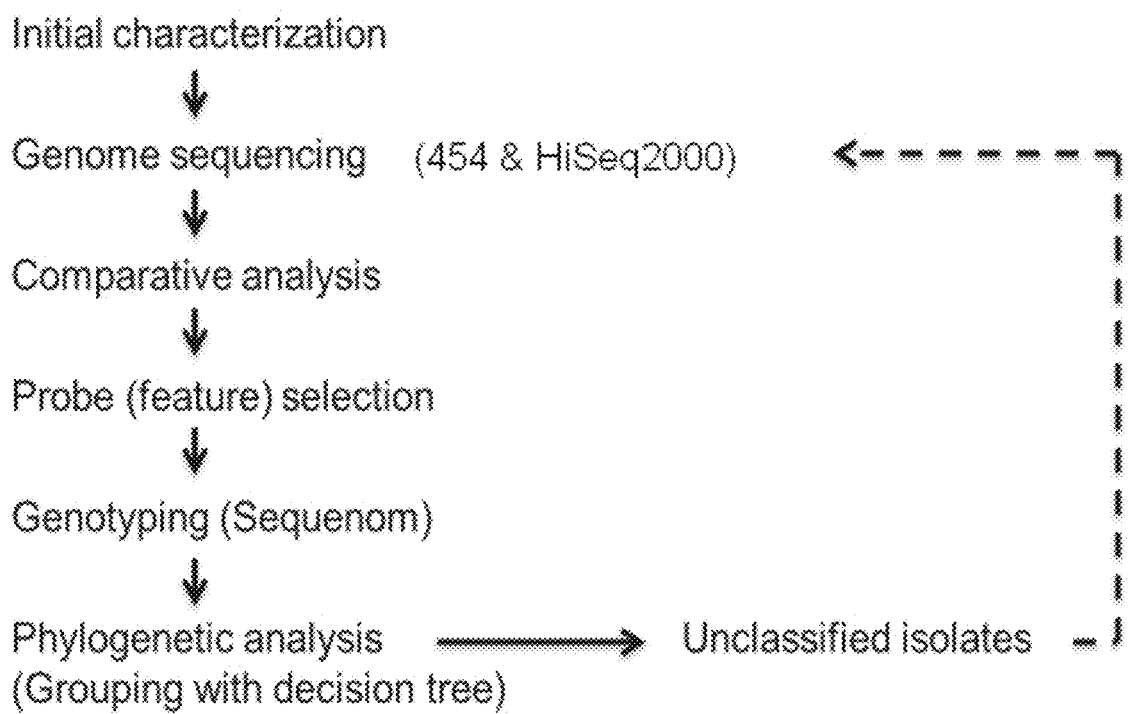
FIG. 1 is an overall scheme for selecting lineage-specific DNA markers.

In the present application, the primer set for genotyping *M. tuberculosis* is selected from the group consisting of primer sets 1-25, each primer set contains a forward primer and a reverse primer. The primer sets 1-25 are shown as follows:

```
Primer set 1:
                                      (SEQ ID No. 1)
ACGTTGGATGTTCTGGACGACCTGTCCTAC
and
                                      (SEQ ID No. 2)
ACGTTGGATGAGCTGCGCCAAGGTTCGTG, Primer set 2:
                                      (SEQ ID No. 3)
ACGTTGGATGTTGTAGCTGCCCAAATTGCC
and
                                      (SEQ ID No. 4)
ACGTTGGATGGGCTTCAATCTCGGCTTGG, Primer set 3:
                                      (SEQ ID No. 5)
ACGTTGGATGTATTCAACACCGGCATCGGG
and
                                      (SEQ ID No. 6)
ACGTTGGATGTCGCCTGGTCGTGGAAGAAC, Primer set 4:
                                      (SEQ ID No. 7)
ACGTTGGATGATCGGACAGCAGAAGGCAC
and
                                      (SEQ ID No. 8)
ACGTTGGATGACTCCCGCGGAACGTGGTG, Primer set 5:
                                      (SEQ ID No. 9)
ACGTTGGATGCAACACCGGCAACTTCAAC
and
                                     (SEQ ID No. 10)
ACGTTGGATGAATTAGCGTCTCCTCCGTTG, Primer set 6:
                                     (SEQ ID No. 11)
ACGTTGGATGTCGAACCCGCCGACAAATG
and
                                     (SEQ ID No. 12)
ACGTTGGATGTCGATTGGTCGCATGCACTG, Primer set 7:
                                     (SEQ ID No. 13)
ACGTTGGATGAAACCTCGGCATAGGGATCG
                                     (SEQ ID No. 14)
ACGTTGGATGTCGACAGGACTATTGGTAGC,
and Primer set 8:
                                     (SEQ ID No. 15)
ACGTTGGATGAAGACGACGGGCCGGATATG
and
                                     (SEQ ID No. 16)
ACGTTGGATGCGTCAAGAGCTTCCCAAATC, Primer set 9:
                                     (SEQ ID No. 17)
ACGTTGGATGCATCCGGGAACACCGTAAAC
and
                                     (SEQ ID No. 18)
ACGTTGGATGATCACCTTCTTATCGGGTGG, Primer set 10:
                                     (SEQ ID No. 19)
ACGTTGGATGCCTGGATTTCAGATATTGCC
and
                                     (SEQ ID No. 20)
ACGTTGGATGTGGCCAGCCCTAGCAAGTC,
```

-continued

Primer set 11:
(SEQ ID No. 21)
ACGTTGGATGAGAACAAACGCGGGATTCAC
and
(SEQ ID No. 22)
ACGTTGGATGTCTCCCGGAGATCACCATTC, Primer set 12:
(SEQ ID No. 23)
ACGTTGGATGGTTGTTTTTGGCCGGGCAG
and
(SEQ ID No. 24)
ACGTTGGATGATCGAGCAGACTCAGCGCTT, Primer set 13:
(SEQ ID No. 25)
ACGTTGGATGTGCTACCGCCAATGTTCAAC
and
(SEQ ID No. 26)
ACGTTGGATGATGGCGTTGACATAACTCGG, Primer set 14:
(SEQ ID No. 27)
ACGTTGGATGATAGCAAGCACGATTGCGAC
and
(SEQ ID No. 28)
ACGTTGGATGACCCCCCGCTGAGGGCGTA, Primer set 15:
(SEQ ID No. 29)
ACGTTGGATGGATTCGATTGGGGAAACGGC
and
(SEQ ID No. 30)
ACGTTGGATGTTCCACATTGGTGATCAGCG, Primer set 16:
(SEQ ID No. 31)
ACGTTGGATGCAAACGGCGTCACTTTGGTC
and
(SEQ ID No. 32)
ACGTTGGATGTGAAATGTGGGCCCAAGACG, Primer set 17:
(SEQ ID No. 33)
ACGTTGGATGCGATTTCGATCGGGATGTTG
and
(SEQ ID No. 34)
ACGTTGGATGCAATCACGATCCCCTCAATC, Primer set 18:
(SEQ ID No. 35)
ACGTTGGATGAGGCAAAGGAAAATCGACCG
and
(SEQ ID No. 36)
ACGTTGGATGTTGACAAACTGAAACACCGC, Primer set 19:
(SEQ ID No. 37)
ACGTTGGATGACAACCGGCCGCAGCGTTT
and
(SEQ ID No. 38)
ACGTTGGATGAAGAACACCGAAAGTGGCTG, Primer set 20:
(SEQ ID No. 39)
ACGTTGGATGTGCATTGGCCACTAAAGCTC
and
(SEQ ID No. 40)
ACGTTGGATGTCGATGACTATCTGCGGATG, -continued Primer set 21:
(SEQ ID No. 41)
ACGTTGGATGACCCATTTGCCGAACGTGTC
and
(SEQ ID No. 42)
ACGTTGGATGTGCTTGGCGACTTTGTGCAG, Primer set 22:
(SEQ ID No. 43)
ACGTTGGATGAGCGTGAAGAAGACGACGA
and
(SEQ ID No. 44)
ACGTTGGATGGTCTGTTGTCATTACGGGAG, Primer set 23:
(SEQ ID No.)
ACGTTGGATGACATCAGGTGATGGTCATGC
and
(SEQ ID No. 46)
ACGTTGGATGCGAAGGGAACAATGGATGTG, Primer set 24:
(SEQ ID No.)
ACGTTGGATGTATGCCAACCGATTTGCCTG
and
(SEQ ID No. 48)
ACGTTGGATGACATATTGTCCACCGCGTAG,
and Primer set 25:
(SEQ ID No.)
ACGTTGGATGTCTTGGCAGCGGCATGGAC
and
(SEQ ID No. 50)
ACGTTGGATGCCGAATTTCCAGTCTCACAG.

The primer set can be applied in polymerase chain reaction to amplify a DNA fragment containing a single-nucleotide polymorphism (SNP) of *M. tuberculosis*. The above primer sets can be used alone or in combination. In some embodiments, the combination of the primer sets can be applied simultaneously in one test tube for PCR test. In some embodiments, any combination selected from the primer sets 1-12 can be applied simultaneously. In some embodiments, any combination selected from the primer sets 13-22 can be applied simultaneously. In some embodiments, any combination selected from the primer sets 23-25 can be applied simultaneously.

In the present application, the extension primer for genotyping *M. tuberculosis* is selected from SEQ ID Nos. 51-75. The extension primers of the present application are listed as follows:

(SEQ ID No. 51)
GACCTGTCCTACGAACCGGTGATGG, (SEQ ID No. 52)
CGTTGCCCACGTTGTTGGCG, (SEQ ID No. 53)
CACCGGCCAACGTCTCGGGCATG, (SEQ ID No. 54)
CCCCCGACCGGCCGTTCTTCG, (SEQ ID No. 55)
TTCAACGGCGGCATCAT, (SEQ ID No. 56)
GCCGAAACAAGATTTGC,

-continued (SEQ ID No. 57)
CCTTCTGCGTCTCCAAT, (SEQ ID No. 58)
GATATGGGGCCGCGGAT, (SEQ ID No. 59)
ACCGTAAACGGGCCTAACCCTCC, (SEQ ID No. 60)
TTGGGGCTGGGAACTGGG, (SEQ ID No. 61)
ATTCACGTGAAAACCCTCG, (SEQ ID No. 62)
AGCTCAGCGCGCGGCTGGTGT, (SEQ ID No. 63)
CAAAATACGGCGATCATCATGGG, (SEQ ID No. 64)
CCACCAGTACTTGCCGC, (SEQ ID No. 65)
ATCGGGGTGACGATGAG, (SEQ ID No. 66)
GCCGAGGAGCCCGCGTAACCGT, (SEQ ID No. 67)
TGTTGATCGGCCCGAGGC, (SEQ ID No. 68)
GCGGGCGTGGAACGCTGGTC, (SEQ ID No. 69)
AGCGTTTCCAGGTCACCGCA, (SEQ ID No. 70)
CCAGAGCGCAACAACAA, (SEQ ID No. 71)
CACGCTGGCATCAAGTTC, (SEQ ID No. 72)
GAAGACGACGAGGACGACTGGG, (SEQ ID No. 73)
GACGATTCCGGGCATGCG, (SEQ ID No. 74)
TGCCTGCCTGGTATGAC,
and (SEQ ID No. 75)
GGCATGGACGGGATCGG.

In one embodiment, the extension primer can be applied in polymerase chain reaction to amplify a DNA fragment having a single-nucleotide polymorphism (SNP) of *M. tuberculosis* as a terminal nucleotide of the DNA fragment. The above primers can be used alone or in combination. In some embodiments, the combination of the above primer can applied simultaneously in one test tube for PCR test.

In the present application, the SNP markers of *M. tuberculosis* are selected from: "T" at position 301 of SEQ ID No. 76, "A" at position 301 of SEQ ID No. 77, "A" at position 301 of SEQ ID No. 78, "G" at position 301 of SEQ ID No. 79, "G" at position 301 of SEQ ID No. 80, "G" at position 301 of SEQ ID No. 81, "C" at position 301 of SEQ ID No. 82, "G" at position 301 of SEQ ID No. 83, "C" at position 301 of SEQ ID No. 84, "A" at position 301 of SEQ ID No. 85, "A" at position 301 of SEQ ID No. 86, "A" at position 301 of SEQ ID No. 87, "G" at position 301 of SEQ ID No. 88, "A" at position 301 of SEQ ID No. 89, "G" at position 301 of SEQ ID No. 90, "G" at position 301 of SEQ ID No. 91, "A" at position 301 of SEQ ID No. 92, "C" at position 301 of SEQ ID No. 93, "C" at position 301 of SEQ ID No. 94, "T" at position 301 of SEQ ID No. 95, "T" at position 301 of SEQ ID No. 96, "T" at position 301 of SEQ ID No. 97, "T" at position 301 of SEQ ID No. 98, "T" at position 301 of SEQ ID No. 99, and "C" at position 301 of SEQ ID No.100. The detail sequence information are shown as follows.

SEQ ID No.76:
TGCCGGGCCGCCTCCAGTCGACGTCGGGTAGTCGCTACCGCCGGCA

CCACCACCCGGCGCACCAGCTGGTCCTGCTCGGCGAATAGCTCGGC

GGCCGCCGCCTCGGCTCGCAATCGTTGTACCCCACCGGTGATCGCG

TTGACCGTCATCACGCCCGCTACCAGTAGCGCGTCGATATTGCTGC

CGACAATCGCCGATGCTGCGGCGCCCACCGCCAGGATCGGAGTCAG

CGGATCGGCCAGTTCATGGCGGGTGGCCACCGCCAGCTGCGCCAAG

GTTCGTGCCGGGCCGCGCAGCGGCTCCATCACCGGTTCGTAGGACA

GGTCGTCCAGAATGCGCCGCCAGGCCGGGATTCCGGGTTCGACGGC

CAAGGGTCGGGAGCCGCCGGCTAGCCGCGAGTAGACGATCTCGGGG

TCCAGCGCGTGCCAGGCGGTCAGCGGTTGCGGGGTGGGGTCGGGCA

TCCGCAGCACCTTGGCGGCCGACCACATTCCGGACACCAAAGCCGT

TGCGGCAGCGGCATTGACCGGATTGAGCCAGCGACGGAAGCTGGCT

GGGTTGGTGGTTTTGTCCTGCTCACCGGTGACCAACAACAGCCCGG

CCA;

SEQ ID No.77:
AGCGTTGGGACCCAGCGAGATGAGGTGCTGCATTTCCAGGGACGCG

ATGACGGCGCTCTGCGAATAGCCGAACACGGTGACGTGGTTTCCGG

CGTTGATTTGCTCCCAAATCGCGCCGTCGAGAATCTGTAGGCCCAA

CTGCACCGAGGTTTGGAAGGGCAGGGATTTGACGCCGGTGATCGGA

TATAGCTCTTCGGGCGTCACCAGCGCTTTGACGACCGGATTCGAGA

CGACGGGGTCGATGAACAAGGTCGTGATGGCGTTGACATAACTCGG

CGTGGGTATCGGTGACCCGGTGCCACCCATGATGATCGCCGTATTT

TGGTTGAACATTGGCGGTAGCACCGGGGGTGAGGTTGGCTTAAAGA

GTCCGGCCGTCGCCTCCTGCACCAGCGCGCTCGTGTTGGTGGCCTC

GGCATTGACAAATGCGTTTGCGGCCGCCGCCAACCTCTGGGTGAAT

TCGTTGTGAAACGCCGCAACCTGTGCGCTGATCGCCTGGAACTGCT

GGCCGTACGCGCCGAACAGCGTGGCAAGGGCCGTGGACACTTCGTC

CGCGGCAGCCGCCGCCAGGCCGGTTGTCGGGGCCGCGACGGCCGCC

GTA;

SEQ ID No.78:
CCGACAACACCGGCCCACCCGGCAGCGTGGTGCTCAGCGAGTTGGC

GGCGTAGAAGGCGGCCTCCGACCGCCATTGCTTGACGTGCACCCCG

GCGGATTTCAGCAGGGTTCGCTGAATCTGGGCGAAGCTGTGCATCG

AGGCGCCCGCGGCTGCCACCGCGGCCAGCAACCACCACCACTTGGC

GCGATACAAGCTCACCCAGGCCTTGGCGAGCTGGTCCCAGCCCAAC

-continued

GCCACCTCTATAGCAAGCACGATTGCGACGATGGCCAGTACCGCCC

ATCGCAACCACCAGTACTTGCCGCACGGGGTACGCCCTCAGCGGG

GGGTGCCCCCACCCGCGTGCGAGGGAGTGCCCCCACGCGCTGGCGG

AGGTTGCGGGCGGGGCGTCGTGCGACACGTGCTTAAGGGTAACCG

TGCAGGTGGCGCCGTAATCGCGATACATCGCTAACCGTGTCAGCCT

CGTTGGGGGGTCGTGACCGGATCGTGCCGCCTGGCAAAGTAACTAT

GCGGGCTCGACGCGACCCGCCGCGACCTTACGACGCCGCCGTTCCC

GTTACGCTTGCCGGATGTCGGCGAGCCTGGATGACGCTTCGGTCGC

ACC;

SEQ ID No.79:
CGAGGCCAGGTTCCAAAAGCCCGAAGCGCCGCCGCCGAAGTTGCCG

AAGCCCGAGGCGGTGCCGGCGCCAGCGTTGAAGAAGCCCGACGACG

GGCTGGTGGTCGAGTTCCCGAAGCCCGGGGCCGCCGGAATCTTGAT

GAGCGGGATGCTGACGCCCCCCACCATGCCGGTGAGGTTGCCGTCG

ATCGTGGTGGTTGGTCCGCCCACGGTGATCGTCACCGTGGGAAGGG

TGAGCGTGGATTGCGGGAGCTCGACCGGGCCGTAGTAAACAACGAA

GGGAACAATGGATGTGAAGGGCAAGCGCATGCCCGGAATCGTCATC

ACGCTTCCGGGCATGACCATCACCTGATGTATCGGCATGCTGAATA

GCTGCGCGTTTATCGGAATGGCGGGAATCTCGAGGGCGATATCGGC

ACCGATCAGGCCTTGGTAGTCGCCCCGCCACAAGACGCCGTTGCTG

TAGTTGCCGGCGATGAAGGCGCCGGTGTTGACGTTGCCGGTGTTGG

CCACTCCAGTGTTGTAGTCGCCGGTGTTGAAGTAGCCGGTGTTGTA

GTTACCTGCGTTGAAGCTGCCGGTGTTGTAGTTGCCGGTGTTGAAG

TTC;

SEQ ID No.80:
TTGAACAACCCGACGTTTCCGCTGCCGGAGTTGAACAGGCCGATGT

TGTGGCTGCCCGAGTTGAAGCTGCCGAACCCGATCTGTCCGTTGCC

GGTGAGCCCGATGCCGACATTGTTGCTGCCCGTATTCCCAAAGCCG

ACATTGTTGCTGCCGGTGTTCGCAAAGCCGATGTTGTGGCCGCCCA

GGTTGGCCAAACCCAGGTTGTCGCTGCCCAGGTTTGCAAAGCCGAG

GTTGTAGCTGCCCAAATTGCCGAAGCCGACGTTGAACACGCCGACG

TTTCCGTTGCCCACGTTGTTGGCGGCGACGTTTGCCAAGCCGAGAT

TGAAGCCCGCCGCGCTCGGGGGGCCGGCAGCGGCTGCCGCGGCGCT

GGTCAGCCGCTCCGATAGGCCCGCCAGCTTCTTCAGCTGCTGGGTG

AACGGCATCAACGCGGAGACGGCCGCCGACGCTCCAGCGTGATAGC

CAACCATCGCGGCCACATCCTGGGCCCACATCCGCTCATAGGCGGC

CTCGGTGGCCGCGATCGCCGGAGCGTTGAATCCCAGCAGATTCGAG

CTCACCAGCGACACCAGCACGGCGCGGTTGGCCGCGACGATCGCCG

GAT;

SEQ ID No. 81:
AGTCGCCGGCGTTGCCGAATCCGAAGTTGTAGCTGCCCAGGTTGCC

TAGGCCGATGTTGTAGTTACCCAGGTTCGCCGGGCCGATGTTGTAT

GAGCCCTGGTTTCCGCCGAAGACGTTGAAGCTGCCGAGGTTGCCGC

TGCCGAGGTTGAAGCTGCCGATGTTCGCCAAGCCGGCGTTGCTGTC

GCCTACGTTGGAGAAGCCGACGTTGAATTGGCCGATGTTTCCCAGG

CCGAGGTTGAACATCGACATCCCGGTCGCCTGGTCGTGGAAGAACC

CCGCGAGGTTGCTGCCGATGTTGAGCATGCCCGAGACGTTGGCCGG

TGCCCCGATGCCGGTGTTGAATACGCCCGAGACGGTATCGCCCAGG

TTCGCCAGTCCCGATTGCAGCGAGCCGTAGTTGTTGAAGCCCGAGG

TCGCGGAGTTCGCGACGTTCTGGAAGCGGAAATGTTGGCGCCGAT

GTTGGCGATGCCCGATACGGTTCCGGGGCCGCCGTTGAAGAAGCCC

GAGGACGGATCGGTGGTGGCGTTGAAAAAGCCCGTGGTAGCCGCAA

TGTTGACGAACGTGACATCGAAGGGACCGACGCTTGCGGTGGCCGG

GAT;

SEQ ID No. 82:
TAAAGCTCAACGGCTACAACACCGCCCAGTTCGGCAAGTGCCACGA

AGTCCCGGTCTGGCAGACCAGCCCGGTCGGGCCGTTCGACGCGTGG

CCCAGCGGCGGCGGTGGTTTCGAATACTTCTACGGGTTTATCGGTG

GCGAGGCTAACCAGTGGTATCCGAGTCTGTACGAGGGCACCACGCC

GGTCGAGGTGAACCGCACGCCCGAGGAGGGTTACCATTTCATGGCG

GACATGACCGACAAGGCCCTCGGCTGGATCGGACAGCAGAAGGCAC

TGGCCCCCGACCGGCCGTTCTTCGCGTACTTCGCCCCGGGCGCCAC

CCACGCGCCCACCACGTTCCGCGGGAGTGGGCCGACAAGTACCGG

GGCCGCTTCGATGTGGGCTGGGACGCACTGCGAGAGGAAACCTTCG

CCCGGCAAAAGGAACTCGGGGTGATCCCGGCGGACTGCCAGCTGAC

CGCGCGGCACGCCGAAATCCCGGCGTGGGACGACATGCCGGAGGAC

CTCAAACCCGTGCTATGCCGGCAGATGGAGGTCTACGCGGGCTTTC

TGGAATACACCGACCACCACGTCGGCCGGCTCGTCGACGGCCTGCA

GCG;

SEQ ID No. 83:
GTTGGCGAAGCCCGAGATTTGTAAATTACCAACGTTTTGGGCGCCG

GAGTTTCCCCTACCAGAATTATTGAAACCCGAATTTCCACTGCCGG

CGTTTCCGAATCCCGAGTTTTCGCCCAGCCCATCGGTAGTATTGCC

GAAACCGGTGTTCAGGTTGCCCGCGTTAAAGCCGCCCGTGTTGATA

TTGCCAGAATTTGCGAAGCCGGTGTTCGTCAGGCCAGAGTTCAAGA

AACCAGAATTAGCGTCTCCTCCGTTGAAGCTGCCTGAGTTGAATGC

ACCCGAGTTGAAGCTACCGGTGTTGATGATGCCGCCGTTGAAGTTG

CCGGTGTTGAAATCGCCCGCGTTCCCTATGCCGGTATTGGCCTGAC

CTGAGTTGCCAAAGCCAGTGTTGACGCTTAACGCGTTCCCGAAGCC

GGTGTTGATAAAGCCGGAGTTTCCGAAGCCGGTGTTGATGTTGCCT

GAGTTGGCTACGCCCGTGTTGGTGACGCCCGAGTTGCCCACGCCGA

AGTTGCCGCTGCCCGAGTTGAAGAAGCCGATGTTCCCGGTGCCCGA

GTTACCAAATCCTATATTACCGCTACCGGAATTCAGTCCGCCAAAG

CCG;

SEQ ID No. 84:
TTGTCCGCAGGAGTGTTGAGTGAGGCGGCCAGCGCCGTGTAGTAGT
CACGGTGACGTGCGTGCACATCGGCCTCGCCGGAGTCGCCCAGTTT
TTCCAGCGCGTACCGACGCACCGTTTCCAGCAGCCGGTACCGCGTG
CGGCCCTGGCAGTCGTCGGCCACCACCAGCGACTTGTCTACCAGCA
GGGTCAGCTGATCAAGCACCGAAAACGGATCCAGGTCGCTACCGGC
GGCGACCGCCCGCACCGCGGCGAGGTCGAACCCGCCGACAAATGGC
GCCAGTCGCCGAAACAAGATTTGCCCGGTCTCGGTCAGCAGTGCAT
GCGACCAATCGATCGAGGCGCGAAGTGTCTGCTGGCGCTGCACCGC
GCCCCGCACACCGCCGGCCAACAGCCGGAAACAGTCGTCCAGACCG
TCGGCAATCTCGAGCGGTGACATCGACCGCACCCGTGCGGCAGCGA
ACTCGATCGCCAGCGGTATGCCGTCTAGCCGCCGGCAGATCTCGCC
GACGGCCGCGGCGTTGTGATTGGCGATGGTGAACCCGGGCTGAACT
CGGCTGGCTCGGTCAGCAAACAATTCGACTGCTTCGTCGGTTATCG
ACA;

SEQ ID No. 85:
TCCAACTCGAAGATTGTTGTCCCGATTGGCCATTGCAATCGGAATG
CACGGGAATCCAATCCTGCAGCCAAGATGACCACCTGCTTCATGCC
GGCGGCCGTTGCCCGGAGAAATACTCGTCGAAATACCTGGTGCGG
GCACCTTGGAAGTTGACGAAATGCTCACCGAAGTCCCCGGTTGTCA
GATAGTGATCGGGCAGCTTGCCGTCCAATACGTCGGCCCATTCACC
ACCTGCGGCACGGCAGAAAACCTCGGCATAGGGATCGATGGCCAGC
GGATCGGCCTTCTGCGTCTCCAATACTCTTGCGGCGGCTACCAATA
GTCCTGTCGAACCAACACTCGTGGTGACATCCCAGCTATCGTCCTC
GGTCCGCATTCATCGAACTCTAGTTGCTCCAGTCCGCCCACCGCTG
TCGGTATCCCAGCGCAGTCGGCCGTGCACACATATCTGCGCGGTGG
ACTTGGTACTTCTACGCGCATTCGCCGATGTTTTGCGATCCGCGGC
GGGTCTATGGTGCCATTTATGTGCCAGGATCGGTCTTCAATAACAA
CGTCGCGAAGCGAGGGGTCGTGACGTGAGAGGGCTCGCTTATGCCG
GCG;

SEQ ID No. 86:
GAGCGCTACCTTGGATGTTGAGGGAGTTGAACTCCGGCGGAAAAAT
TGTGAAATCCATTGTCGCTCAACCGCTGTCTAGGTGGAGGTGCCCG
CGCGGTTGGCTAATTCGGTGAGCCAATACGAAGTCTTGCTGGTCTG
AAGTGTTTGGACAAATGACTCGTGGATCACATGGGCCTGGCGCGCG
ATCGCCTTGTACAGCTCGCCGTGCATGGAAAACAGCATCGACGTCA
CGATGGACACAAGATCGTGGGCGGGGGATTCCACATTGGTGATCAG
CGGCGTGACCCCGTCATCATGGGCACTCATCGTCACCCCGATCTCG
TGGAGGTTGGCGGCCGTTTCCCCAATCGAATCGGGCCGTGTGGTGA
CAAAAGACACGCGTGCATCTCCTTCCACTGACGTGGTCTGATGGTG
GGGGTCAGCGACGACTTGGGGTTCCGCACGGCATTGTAGACGGAAT
CGTTCACTAAGGTATTTTCACCATAACGGCTTCGGTCACAAAACGG

TAGCGATTCTGTTGAGGAATTTTTTCGACGCTCGCCCGGTAGGGTG
CCTCCATGTCTGAGACGCCGCGGCTGCTGTTTGTTCATGCACACCC
CGA;

SEQ ID No. 87:
TCTGTGGGTGGTCCCGGATGTCGCGGCCCGCGGAGCCGATCTTGCC
CATGTCCCAGTGGTGACGCTGGTCGGAAGCGCCCGGCACTATTGGG
GCGCGGTGGCGGCGGTGTTGGCGGCAGTGTGTGCTTTGCTCGCTGC
CGTCTTCTTGATGAGTTCGGCGGCGATTCGCGGGTCGGCTGGCGAG
GACATGGCGAGATATGCGGCGCCCCGCGCCCGCCGGTCGATTGCCC
GGCGCCAGCACTCGAATGCGGCCGGCCGGGCGGCTCCGCAAGACGA
CGGGCCGGATATGGGGCCGCGGATATCGGAGCGAATGATTTGGGAA
GCTCTTGACGAGGGCCGTGACCCGACCGATCGGGAGCAGGAGTCTG
ACACCGAGGGGCGGTGACGGACCGCGCGCTGACGGTCGCTACCCTT
CATGGACGTCGTCGAAATTGACGAGCGCGTGTGGGTGACAGTGGGA
AGGGAACGGCAGGCATGAGTCCGGCAACCGTGCTCGACTCCATCCT
CGAGGGAGTCCGGGCCGACGTTGCCGCGCGTGAAGCCTCGGTGAGC
CTGTCGGAGATCAAGGCTGCCGCCGCTGCGGCGCCGCCGCCGCTCG
ACG;

SEQ ID No. 88:
AACCCACGGTGTTGTAAAACAGCTGTGATATCGGCAGATACCAGTT
GATGAACCATTCCAGCCACCCCGGGGTCGCGGCGGCGGTCAACGCG
GACGACAGGGGCGAGGTGAGGCCCAGCAGCGTGTTGGGCAAGTGGG
CGATCAGCTCCGCTATTGCGCTCTGCGCCGCGCCGGCTGAGGTGCC
GGCGGCTTTGGCGACTGCGGACAACTGCGTCGCCGCGGCGGATGGG
CTGGTGGTGTTCGGCGGCGGGCAAACGGCGTCACTTTGGTCGCGG
TCGCCGAGGAGCCCGCGTAACCGTGCATGGCCATGGCGTCTTGGGC
CCACATTTCAGCGTATTGAGCTTCGGTGGCCGCGATTGATGCGGTG
TTTTGACCGAACACGTTATGCGTGACCAGCGACGTGAGCCGCGCGC
GATTGGCCGCGATCAGCGGCGGGGGCACAATGGCGGCAAACGCGGT
TTCGTAAGCGGCCGCCGCCGCACGCGCCTGACTGGCTGCCTGCTCA
GCTTGGATGGCGGTGGCTCGCATCCACGCCACATACGGGGCGACCG
CTTCGACCATCAACGTCGACGCCGGACCCAGCCATTCTTCGGTTTG
CAG;

SEQ ID No. 89:
CCGGCCACCTGTGGCACCAGCGTCTATGTCTACCCATTCGACCTTG
CCGACGAGGTCTTTACCTGGGCCCGCGCGGTCAGCGCCGAAGTCGA
CCCTCGGGTCGAGCTGCAAGCCCTTGCCTCCCGCGGTGAACCGAGC
ATGGGCATCGACGTCCCCGTCATCTCCCTTGCCTCGCCCGCTTTCG
CTGACTCGCCCGAAGAGGCCGAACAGGCCCTCGCCCTGTTCGGCAC
CTGCCCGGTTGTCGAGCAGGCACTGGTCAAAGTCCCTTATATGCCA
ACCGATTTGCCTGCCTGGTATGACATCGCGATGACCCACTACCTGT
CAGACCATCACTACGCGGTGGACAATATGTGGACGTCGGCGTCCGC

TGAGGACCTGCTGCCGGGTATCCGCTCAATCCTGGACACGCTGCCC

CCGCATCCGGCGCACTTCCTCTGGCTGAACTGGGGTCCATGCCCTC

CCCGTCAAGACATGGCCTATAGCATCGAAGCCGACATCTACTTGGC

GCTCTACGGCTCCTGGAAGGATCCGGCCGACGAGGCGAAGTACGCC

GACTGGGCGCGGTCCCACATGGCCGCGATGTCGCATCTGGCGGTCG

GCA;

SEQ ID No. 90:
TGTTACCGACGCCGGAGTGAAAGGCCGATGTCGCTAGGCCCAGCGT

GCTGGTGTTGTAGAGGCCTGAGACTGTGTTGCCGAAGTTCAAGATT

CCCGATGTCAGTGGCCCGACGTTAAGGAATCCGGAGTTGCCGAGAT

TCCCAGCAATGTTCCAGAAGCCAGATCCGCCCGAACCGACGTTCCC

GAAACCCGATGTGCCGCCCGTACCGCTGTTGAAGAAGCCCGATGAC

GGGGTGGTGGTCGAGTTTCCGAAGCCTGGGGTGCCCGCGATTTCGA

TCGGGATGTTGATCGGCCCGAGGCGGCCGGACACGTCGATGCCCAA

CGGGATTGAGGGGATCGTGATTGGCGGGGTAGTGAGGGGGCCGATG

GCGCCGCCCACATCAATACCCAACGGGATTGCCGGAAGTGAGTAGC

CATCCGGGAACACCGTAAACGGGCCTAACCCTCCGCCCACATCAAT

ACCCAACGGGATTGCCGGAAGTGAGTAGCCATCCGGGAACACCGTA

AACGGGCCTAACCCTCCGCCCACATCAATACCCAACGGGATTGCCG

GAAGTGAGTAGCCATCCGGGAACACCGTAAACGGGCCTAACCCTCC

ACC;

SEQ ID No. 91:
GCTGCCGGACACGTCGATGCCCAACGGGATTGAGGGGATCGTGATT

GGCGGGGTAGTGAGGGGGCCGATGGCGCCGCCCACATCAATACCCA

ACGGGATTGCCGGAAGTGAGTAGCCATCCGGGAACACCGTAAACGG

GCCTAACCCTCCGCCCACATCAATACCCAACGGGATTGCCGGAAGT

GAGTAGCCATCCGGGAACACCGTAAACGGGCCTAACCCTCCGCCCA

CATCAATACCCAACGGGATTGCCGGAAGTGAGTAGCCATCCGGGAA

CACCGTAAACGGGCCTAACCCTCCGCCCACATCAATACCCAACGGA

ATAGCCGGCAAACTATAACCACCCGATAAGAAGGTGATGGGACCGA

TTTGACCACTCACTGTCACGTAATCTGGAGGGAATCCGGGGAAAAA

TGGCGGAATCGCGGGAATCTCAGGAGTGCCTAGCTGTATCGATATG

CTACCCGGGCCTATGCTGCCAACGGTGGGATTTACGCCGAATAAGC

CGATCGCAAGCGGAGACGCGGGGATCGAAATCGATCCCACGTTAAT

GACCTGGAACGCCGATAGCTCTAGGCCAATAGAATTTAGAGTGATC

GGC;

SEQ ID No. 92:
CCATGCGGTGCCGCGGTGGTCCAGCCAGCGCCCTGCAGTGTGCTGG

TGCTCGATACCAGGTTGGCCTGTCCCGCCCAGCTGGGCGGCACCGA

CAATGCGCCGATTGACGACGCCCGACTAAGGCCGGCGGCTAGCGGA

GCCGCACCCAGACCGGCCGCGATCGGCGCCTCGCCGACGGCCGCCT

CCGCCGCCCCCAGCTCCGATAGGCCCGCGCCCTCCAAGCCCTCCTC

GAGGGCGGCTTCCTCGGCAGCCGGAAGAAGACCACCGCTGGCCAGC

CCTAGCAAGTCCGACGCGGCGGAGACCCAGTTCCCAGCCCCAATGT

TGAAGATATTGGCAATATCTGAAATCCAGGAGGGCACCTTCCCGGG

CGTGGAACCCAAGATGCTCGCGATACCCGACAACGGCGAAGCGGCC

GCGGATGAGTTGGCGGCCTCGGTGGCCGCATAGGTGCCAGCGCTGA

CCCCCAGGGTCTTCACAAACAGGTCGTATACCGCAGCTGCTTCAGC

ACTGACCTGCTGGTAGAGAGTGCCGTACGCGGTGAACAACGGCGCC

TGTAGCACTGATATCTCATCAGCGGCGGCGGGAATCACGCCCGTGG

TGG;

SEQ ID No. 93:
ACGTCGAGCCAACCCCACTTCAGTGGGTAGGTGAACTCGTCCAGCA

GATAGAAGTCGTGACGTTGCGTGGCCAGCCGGAGCGCGATCTCGGC

CCAACCGTCCGCCGCCGCGGCCGCACGATCGACGTCGGTGCCGGCC

TTGCGAGACGTACGTGTCCAGGACCAGCCCGCACCCATCTTGTGCC

ACTCCACCGCTCCGCCGATCCCGTGCTGGTCGTGCAGCCGGCCCAG

TTGACGAAACGCCGCCTCCTCACCCACTTTCCACTTAGCGCTCTTG

ACAAACTGAAACACCGCGATGTCCCGACCAGCGTTCCACGCCCGCA

ACGCCATTCCGAACGCCGCGGTCGATTTTCCTTTGCCTTCACCGGT

GTGTACCGCCAGTATCGGCATGTTGCGCCGGGCCCGGGTGGTCAGG

CCATCGTTGGGCACTGCGAGCGGATTGCCCTGCGGCATGTGTGGTT

ACCTATCCATCGTCAAGCCACGCCACGCACGGCATGCACTAGATAA

TCCGCGTGCAACTGCTCCAACCGAACCACCGGCGCACCCAGCTGAC

GAGCCAGTTGCGCTGCCAAACCCAGCCGTACATACGACGTTTCGCA

GTC;

SEQ ID No. 94:
CTGCGAGTGGGCCGACCGATAGGCCCGATGCTGGCACAGACCGCGA

CCAGCGTCCATGATGCACTCGAACGTCACGGCGGCACAACCATTTT

CGAGGCTAAACTAGACGGCGCGCGAGTGCAGATCCACCGGGCAAAC

GACCAGGTCAGGATCTACACCCGAAGCCTGGACGACGTCACTGCCC

GGCTGCCCGAGGTGGTGGAGGCAACACTGGCACTGCCGGTCCGGGA

TCTAGTGGCCGACGGCGAGGCGATCGCGCTGTGCCCGGACAACCGG

CCGCAGCGTTTCCAGGTCACCGCACCACGGTTCGGCCGATCGGTCG

ATGTTGCGGCTGCCCGCGCGACGCAGCCACTTTCGGTGTTCTTCTT

CGACATCCTGCATCGGGATGGTACCGACTTGCTCGAAGCGCCGACC

ACCGAGCGGCTGGCCGCCCTGGACGCACTGGTGCCGGCTCGGCACC

GCGTGGACCGGCTGATCACGTCCGATCCAACGGACGCGGCCAACTT

CCTGGATGCGACGCTGGCCGCCGGCCACGAGGGGGTGATGGCCAAG

GCACCGGCCGCTCGTTACCTTGCGGGTCGCCGCGGGAGCGGGCTGGC

TGA;

SEQ ID No. 95:
ACGGTGAGGCCGGCCGGGAACAAGGCCAAGGACGATGTGGACAGAT

TGAAAGTCGCGCCGAACGGGCCGGGGATCGTGCCCGGGCCGCCGTA

GCTGCCGATGATGGGTCCATTGATCTGCAGGTCGCTGATGCTGAGG
TAGAACGACCCGGAGGGGAATTTCGCGCGGGTGGGCCTAGCGGCG
GGCCGTAGTGGTCGATCGTGATGAACGGGTCCGGCAAGACGACCG
GTCCGCGGTGATTTCTGCCATGGCGGTTTGCCCGAAAAGAACAAAC
GCGGGATTCACGTGAAAACCCTCGTGGCCGACGGTTCCGGTCACGT
GGATCGGGATCGCGGGAATGGTGATCTCCGGGAGAGTGAATTCGCG
GATCCCGATGAATCCCCGGTGATTTGTATGTCGAATGCCGGAATA
TCGATGGGCTGGACGTGGATGGGACCGATCCCGCCAATCACCTGCA
GGTCAATGGGGATTTCGGAAATGGTGAAAAGGGTGCCGGGGGTGAA
GGGGGCCAGGACGTTGATGTTGTTGCCCGTTAAGAAGAAACCGGTG
TTGTGGCTTCCCGAATTGAATACGCCCAAATTCCCGGTGCCGGAGT
TGA;

SEQ ID No. 96:
ACAAGCGCGGTAGCCCGCTCGACATCGCTTGCTGTCATTGCGGCAG
GTGCTTGATAGAGGGCCGCCAATTCGGTCGCCGCTTCGGATCGCGA
GTTCAGGGCGGCAACAACTGGCAGTGTCGCCTTACGTCGGGCAAGG
TCGTTGCCGACCGGCTTTCCCGTCACACCAGGGTCACCCCAGATGC
CGATCAGATCGTCGACGCATTGAAACGCAAGACCCAACTCATGGCC
AAAACGCTCCAACGCAGCAATCGTCGCGTCGTCTGCATTGGCCACT
AAAGCTCCCAGAGCGCAACAACAATCGGTCAGGGCGGCCGTCTTGC
CCGCGGCCATCCGCAGATAGTCATCGACTGTAACTTCGGGCTGTCC
CTCCAATAAACAATCCTCAAACTGGCCGATACACAAGTCCAGGCAC
GACATCTGCAATCGCCTTATCGCCCTGACCGCCACACACTCGTCGG
TCAGGCCGGTCAGTATCCGAACGGCCGTGGCGTGCAACGCATCTCC
CAACAGGATCGCGACGCCCACACCCCACACACTCCATACCGTCGGC
CGTCCCCTGCGAGTCGCATCCCCATCCATCACATCGTCATGCAACA
ACG;

SEQ ID No. 97:
GTCAGCCAGTCGTTGCGAACATCGTCGTCCACGTAGGGCTGTATCT
GTTGGCGAACCACTTCGACGGCCGTCGGCCGATCTGCCCCCTCCGT
CGTGAGCGCTTCGGCCGCAGCCAACCATGCCGGCCGCTGCGCCAGG
GCACGCTCGTCGATCGAATGGCCGTCGCGACTTTGGAGTCCACCAG
CTGCCAGAGGTTGTCGCGCAGCGATTCGCAGCGTTGGGCCGCGGCA
CGGACTTCGGTGACCACCGAATTTCCAGTCTCACAGTGACGCTGCA
CAAAGTGCACCGCCGCGTCGGCCTCCGATCCCGTCCATGCCGCTGC
CAAGACGGCGACCTGGCTACGCTCCATCCGCAGCGCCTCCATGAGC
ACACTGGCGGCAGCCCGCAGCTGCGCGCAGTCAGCGTCGAGCGCGT
GCAGGTCAAGTCCGTCTTCGCTGCCGTACCAGTCGTGGATCTGGGC
AGGGTAGGCGGTCAGGTCGGGATGTTGGTAGCCCACCAGGTGGCAA
GCCCGCACGTAGCTTTGCGTGTGCTCGGCTGCGGGCCTGCCCTCGG

CGAGACGCTCAGCGACGTTCAACCGGTCAGCCACCCTCACCCGATC
CG;

SEQ ID No. 98:
CGCCAGCACCGCGGGGCTCGCCGCCGGGGTCGTGGCGGTCCAAACG
GCCGGAACCTTCAATCCCCCGACCGACGCCGCCTGACCGACGGCGC
CCGCAACGCCGCTCAGGCCAGCACTCGGAATGGCCGGAACGGCGGC
CGGCAACGCCTTGGCGGCCTCACCGGCGGCTTTGGCGCCTTCACTC
GCCCACTTCGGCAGGTCGTGCGCCAGGCCAAAGTAGTCCTTGAATT
GGGTGACCATGAGCCGAGCGGGCGAGACCCATTTGCCGAACGTGTC
CATGGCCACGCTGGCATCAAGTTCTGCCGACCCGGTCACACCCTGC
ACAAAGTCGCCAAGCACTCCGCCCACGATGAGCCCGCTACCGTCCG
AGGACCAGGTGTGCCCGGTCAAACCGAGCGCCTTGCCAAGGTCGGT
GAGCCAAGGCGGTTCATTGGTGAAGATTCCGCTAAGCCCAAACAAC
GCTTTAGGAATGTCGGTGAGTGCTTGCGCATTTGCGGCCCCGCTGA
CAGCTTGTCCGACAGATGCGGCCTGGCTGGCCAGCCCGGCCGGGTT
GATGGTCTGCGCCGCCGGATTGAATGGCGACAACTGCGTCGCCGCC
GCC;

SEQ ID No. 99:
TGCGCGATGCCGACGATGCCGCGCTGCTTGCCGCAATCGAGGACTG
CGCGCGTGCCGAGGTGGCCGCCGGCGCCCGCCGCCTGTCAGCGATC
GCCGAACTCACCAGCCGGCGCACCGGCAATGACCAGCGGGCCGACT
GGGCGTGCGACGGCTGGGACTGCGCGGCCGCCGAGGTGGCCGCCGC
ACTGACCGTAAGCCACCGTAAGGCCTCCGGGCAGATGCATCTGAGC
CTCACCCTAAACCGACTGCCCCAGGTGGCGGCGTTGTTTTTGGCCG
GGCAGCTCAGCGCGCGGCTGGTGTTGATCATCGCCTGGCGCACCTA
CCTGGTTCGCGACCCCGAAGCGCTGAGTCTGCTCGATGCCGCCCTC
GCCAAACACGCCACAGCGTGGGGTCCGCTGTCGGCCCCCAAACTGG
AAAAGGCTATCGACTCCTGGATTGATCGGTACGATCCCGCCGCACT
GCGACGCACCCGTATCTCGGCCCGCAGCCGCGACCTGTGCATCGGT
GATCCCGACGAAGATGCCGGCACCGCCGCACTATGGGCCGGTTGT
TTGCCACCGACGCCGCCATGCTGGATAAGCGCCTCACCCAGCTGGC
CCA;
and SEQ ID No. 100:
ATCCGCTGGCTGGTGGATCAGGCCCCAGCGCGGGCGCGGGCCTGCT
GCGCGCGGAGTCGCTACCTGGCGCAGGTGGGTCGTTGACCCGCACG
CCGCTGATGTCTCAGCTGATCGAAAAGCCGGTTGCCCCCTCGGTGA
TGCCGGCGGCTGCTGCCGGATCGTCGGCGACGGGTGGCGCCGCTCC
GGTGGGTGCGGGAGCGATGGGCCAGGGTGCGCAATCCGGCGGCTCC
ACCAGGCCGGGTCTGGTCGCGCCGGCACCGCTCGCGCAGGAGCGTG
AAGAAGACGACGAGGACGACTGGGCCGAAGAGGACGACTGGTGAGC
TCCCGTAATGACAACAGACTTCCCGGCCACCCGGGCCGGAAGACTT -continued

GCCAACATTTTGGCGAGGAAGGTAAAGAGAGAAAGTAGTCCAGCAT

GGCAGAGATGAAGACCGATGCCGCTACCCTCGCGCAGGAGGCAGGT

AATTTCGAGCGGATCTCCGGCGACCTGAAAACCCAGATCGACCAGG

TGGAGTCGACGGCAGGTTCGTTGCAGGGCCAGTGGCGCGGCGCGGC

GGGGACGGCCGCCCAGGCCGCGGTGGTGCGCTTCCAAGAAGCAGCC

AAT.

The above SNP markers of *M. tuberculosis* are correspondent to "T" at position 128290 of genome of the reference strain, "A" at position 178812 of genome of the reference strain, "A" at position 243118 of genome of the reference strain, "G" at position 374353 of genome of the reference strain, "G" at position 375095 of genome of the reference strain, "G" at position 430332 of genome of the reference strain, "C" at position 756840 of genome of the reference strain, "G" at position 848652 of genome of the reference strain, "C" at position 991896 of genome of the reference strain, "A" at position 996219 of genome of the reference strain, "A" at position 1300047 of genome of the reference strain, "A" at position 1810066 of genome of the reference strain, "G" at position 1932201 of genome of the reference strain, "A" at position 2008738 of genome of the reference strain, "G" at position 2165256 of genome of the reference strain, "G" at position 2165554 of genome of the reference strain, "A" at position 3078579 of genome of the reference strain, "C" at position 3157993 of genome of the reference strain, "C" at position 3426415 of genome of the reference strain, "T" at position 3734189 of genome of the reference strain, "T" at position 3797876 of genome of the reference strain, "T" at position 3859376 of genome of the reference strain, "T" at position 4061113 of genome of the reference strain, "T" at position 4221423 of genome of the reference strain, and "C" at position 4352162 of genome of the reference strain, respectively.

In the present application, the reference strain is *M. tuberculosis* H37Rv having a complete genome sequence NC_000962.2. Said genome sequence is public information, which is published in the database of National Center for Biotechnology Information (NCBI) entitled "gi57116681/ref. NC_000962.21 *Mycobacterium tuberculosis* H37Rv chromosome, complete genome".

Table 1 shows the detail information of the SNP markers of the present application. In Table 1, the H37Rv genome position indicates the position of each SNP marker in the reference chromosome, the reference allele indicates the nucleotide exist in *M. tuberculosis* H37Rv strain, and the variant allele is the SNP marker of the present application.

TABLE 1

SNP markers of *M. tuberculosis*

| SEQ ID No. | varID | Correspondent H37Rv genome position (NC_000962.2) | reference allele | variant allele |
|---|---|---|---|---|
| 76 | 94 | 128290 | G | T |
| 77 | 128 | 178812 | G | A |
| 78 | 164 | 243118 | G | A |
| 79 | 246 | 374353 | A | G |
| 80 | 247 | 375095 | C | G |
| 81 | 270 | 430332 | A | G |
| 82 | 450 | 756840 | T | C |
| 83 | 503 | 848652 | A | G |
| 84 | 570 | 991896 | T | C |
| 85 | 573 | 996219 | G | A |
| 86 | 732 | 1300047 | G | A |
| 87 | 998 | 1810066 | G | A |
| 88 | 1060 | 1932201 | A | G |
| 89 | 1093 | 2008738 | G | A |
| 90 | 1181 | 2165256 | T | G |
| 91 | 1182 | 2165554 | A | G |
| 92 | 1626 | 3078579 | G | A |
| 93 | 1673 | 3157993 | A | C |
| 94 | 1799 | 3426415 | T | C |
| 95 | 1943 | 3734189 | A | T |
| 96 | 2000 | 3797876 | C | T |
| 97 | 2035 | 3859376 | C | T |
| 98 | 2137 | 4061113 | G | T |
| 99 | 2236 | 4221423 | C | T |
| 100 | 2329 | 4352162 | A | C |

In some embodiments, various genotypes of *M. tuberculosis* possess various combinations of the SNP markers. Preferably, the combination of the SNP markers contains at least two markers, such as 3, 5, 7, 10, 15, 20, or 25 markers. However, in some embodiments, the above SNP markers may used alone.

The present application also provides a method for genotyping *M. tuberculosis* comprising obtaining a sample, amplifying and obtain at least one of first DNA fragment by using one or more primer sets selected from the group consisting of primer sets 1 to 25 (SEQ ID Nos. 1 to 50), amplifying and obtain at least one of second DNA fragment by using the obtained first DNA fragment as template and using one or more extension primers selected from the group consisting of SEQ ID Nos. 51 to 75, and detecting the second DNA fragment by using mass spectrometry.

In some embodiments, the method can further comprises analyzing the mass spectrometry data based on the single-nucleotide polymorphism markers selected from Table 1.

In one preferred embodiment, the mass spectrometry is matrix-assisted laser desorption ionization time-of-flight mass spectrometry (MALDI-TOF MS).

Examples of the suitable sample applied for the method can include, without limitation, bacterial culture, nasal mucus, phlegm saliva, blood, section of tissues or organ, biopsy and the like.

The present application further provides a kit for genotyping *M. tuberculosis* comprising at least one primer set selected from the group consisting of primer sets 1 to 25 (SEQ ID Nos. 1 to 50), and at least one extension primer selected from the group consisting of SEQ ID Nos. 51 to 75. In some embodiments, the kit may further comprises a database of genotypes of *M. tuberculosis* based on single-nucleotide polymorphism markers, preferably, based on the SNP markers shown in Table 1.

Examples

To investigate the transmission, virulence, antimicrobial resistance and other attributes of the MTB, the inventors sequenced the genome of six strains isolated in Taiwanese population using next-generation DNA sequencers (Roche 454/Illumina GAIIx). Based on the comparative genome analysis, there were 60 and 141 strain-specific single nucleotide polymorphisms (SNPs) found in PE/PPE and non-PE/PPE gene families, respectively, comparing to the H37Rv reference strain. In the present application, lineage specific SNPs were used as markers to design a novel strain classification scheme and conduct the phylogenetic analyses. The performance of this genotyping panel was compared with the current standard test, spoligotyping patterns specific for 156 Mycobacterium tuberculosis complex (MTBC) isolates.

Materials and Methods

Bacterial Strains and Molecular Typing

MTB isolates were collected between 2004 and 2007 from the mycobacteriology laboratories of five general hospitals located in four geographical regions in Taiwan, namely, Taipei Tri-Service General Hospital (northern region), Mennonite Christian Hospital (eastern region), Wan-Ciao Veterans Hospital (central region), Tainan Chest Hospital (southern region), and Kaohsiung Veterans General Hospital (southern region). The bacterial strains used in this study are representative of the diversity of MTB in Taiwan as shown previously (Chang J R et al., Clin Microbiol Infect 2011, 17(9):1391-1396; Dou H Y et al., BMC Infect Dis 2008, 8:170; Dou H Y et al., Infect Genet Evol 2008, 8(3):323-330; Dou H Y et al., J Microbiol Methods 2009, 77(1):127-129). Spoligotyping and MIRU-VNTR genotyping assays were performed based on internationally standardized protocols. A total of 156 isolates (of the Beijing, EAI, Haarlem, LAM, T, MANU, and unclassified strains) that had all genotype data available were used for the subsequent analyses.

Genome Sequencing of MTB Strains

Six MTB strains, W6, M3, M7, A27, A18 and M24, belong to the genogroups modern Beijing, Haarlem, Latin-American Mediterranean (LAM), T, East African-Indian (EAI), and ancient Beijing, respectively. They represent the major types of clinical strains isolated from three different ethnic groups in Taiwan and were taken to whole genome sequencing using the 454 pyro-sequencing approach (Margulies M et al., Nature 2005, 437(7057):376-380). TB strains were sequenced 14 to 28-fold depth of the genome separately using a Genome Sequencer 20 (GS-20) or a Genome Sequencer FLX (GS-FLX) instrument (454 Life Sciences, Roche) with a 500-800 base-pair shotgun library for each strain.

DNA libraries of six MTB Haarlem and six T clinical isolates were prepared using Nextera DNA sample preparation kit (Illumina, Calif., USA), and were multiplex sequenced (2×100 bp) at one lane of flow cell using HiSeq2000 sequencer. After performing de-multiplex procedure, the average sequence size of each sample was 3.38 Gb, and the depths of these samples were ranged from 568 to 1068-fold when mapping to H37Rv reference sequence, resulting in that the reference coverage of these samples was from 99.44% to 99.82%.

Mapping to the Reference Genome H37Rv

The 454 sequencing raw data (sff files) from each strain were collected into a specific folder as the read source to align the reference genome of the strain H37Rv. H37Rv genome sequence and the annotated gene information were downloaded from the NCBI ftp site for Microbial Genome Assembly/Annotation Projects. 454 GS Reference Mapper (Roche) software (version 2.3) was used to map 454 reads to the reference sequence (see Table 2 for detail information) and generate high-confidence variations between the reference and each of our six MTB clinical strains.

TABLE 2

Statistics of lineage-specific single nucleotide polymorphisms (SNPs)

| | | # of lineage-specific SNPs | PE/PPE gene family | | non-PE/PPE gene family | | |
|---|---|---|---|---|---|---|---|
| Isolate | Lineage | | synonymous SNPs | non-synonymous SNPs | synonymous SNPs | non-synonymous SNPs | intergenic SNPs |
| M3 | Haarlem | 133 | 3 | 3 | 55 | 56 | 16 |
| W6 | modern Beijing | 270 | 4 | 7 | 78 | 150 | 31 |
| M7 | LAM | 317 | 10 | 7 | 93 | 163 | 44 |
| A18 | EAI | 1,260 | 37 | 60 | 368 | 639 | 156 |
| A27 | T | 136 | 2 | 2 | 48 | 69 | 15 |
| M24 | ancient Beijing | 260 | 6 | 10 | 78 | 138 | 28 |
| | Sum | 2,376 | 62 | 89 | 720 | 1,215 | 290 |

Selection of Strain-Specific SNPs

Based on the result which contains "High-Confidence" differences with at least three non-duplicate reads that (a) show the differences, (b) have at least five bases on both sides of the difference, (c) have few other isolated sequence differences in the read, and (d) have at least one aligned in the forward direction and at least one aligned in the reverse direction. Besides, only those variation sites that all six strains have at least three reads covered and the variation rate larger or equal to 80% were considered as valid. Home-made scripts were used to merge the mapping results of all six strains and parse those valid differences into a MySQL database for further analysis. Strain-specific (observed only in single strain) SNPs were selected and grouped into two categories: PE/PPE protein family and non-PE/PPE. According to the location of the variations, they can be synonymous or non-synonymous to the coding sequences. And in non-PE/PPE group, the variations can also locate at non-coding sequences, which are intergenic regions. To further confirmation using MassARRAY Analyzer (Sequenom), the number of the variations was reduced with criteria that both total depth and variation depth must larger than 15 and the variation frequency must larger than 90% for each variation site.

For SNP calling of Illumina HiSeq2000 sequence data, mapped sequence data of each sample was analyzed using CLC Genomics Workbench software (Aarhus, Denmark) with default parameters. We applied an additional filter to identify highly reliable SNPs with more than 30-fold depth and >95% variant frequency.

SNP Genotyping Based on the MassArray System

PCR and extension primers were designed for 60 PE/PPE and 60 randomly-selected non-PE/PPE SNPs using the MassArray Assay Design 3.1 software (Sequenom, San Diego, Calif.). Five of them were excluded due to difficult sequences. PCRs contained, in a volume of 5 ul per well, 1 pmol of the corresponding primers, 5 ng genomic DNA, and HotStar reaction Mix (Qiagen) in 384-well plates. Three wells were needed for each sample. PCR conditions were as follows: 94° C. for 15 min, followed by 40 cycles of 94° C. (20 s), 56° C. (30 s), 72° C. (60 s), and a final extension of 72° C. for 3 min. In the primer extension procedure, each sample was denatured at 94° C., followed by 40 cycles of 94° C. (5 s), 52° C. (5 s), 72° C. (5 s). The mass spectrum from time-resolved spectra was retrieved by using a MassARRAY mass spectrometer (Sequenom), and each spectrum was then analyzed using the SpectroTYPER software (Sequenom) to perform the genotype calling. After analyzing the genotype profiles, the clustering patterns of five SNPs could not be used to correctly perform genotype calling, and the data of 110 SNPs (57 PE/PPE and 53 non-PE/PPE) were finally used in the following analyses.

Linkage Disequilibrium and Phylogenetic Analysis

Figure 2:
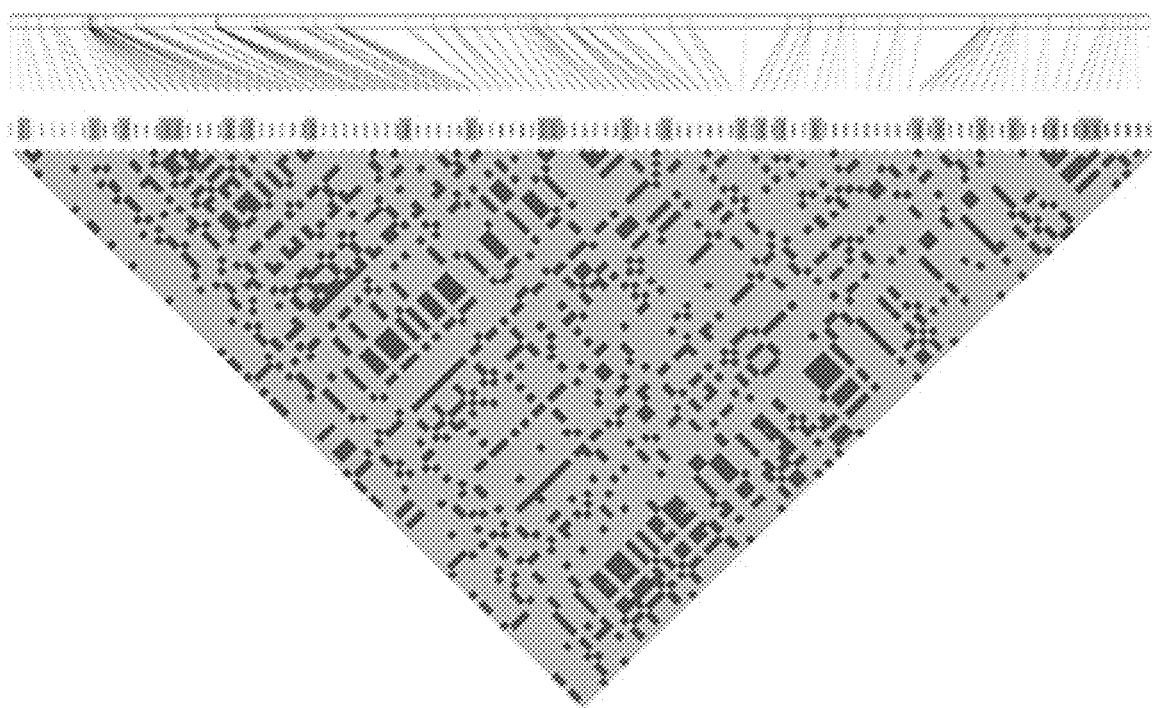
FIG. 2 illustrates linkage disequilibrium of SNP markers in the MTB genomes. The LD plot was created using Haploview software, and the color code on plot followed the standard color scheme for Haploview: blue indicates |D'|=1 and LOD<2, and bright red indicates |D'|=1 and LOD≥2.

Based on the haploview software, the Lewontin D' measure was used to estimate the intermarker coefficient of linkage disequilibrium (LD) as shown in FIG. 2. An extra stringent criteria, r2=1 between each pair markers, was used to select 25 tagSNPs from 110 SNPs. We applied the Phylip software to calculate the Nei's distance using SNP data, and then constructed a phylogenetic tree using the neighbor joining approach.

Results

Genome Sequencing of Six MTB Clinical Isolates

The overall scheme for selecting lineage-specific DNA markers is shown in a flowchart (FIG. 1). Based on our previous study of the MTB stains in Taiwan (Dou, et al), we selected representative strains for whole-genome sequencing. The initial grouping of these bacteria was based on spoligotyping and MIRU, also we consider the ethnic background of the patients that were infected with MTB. We applied whole-genome shotgun approach to generate high coverage sequences using the 454 technology. Genome sequence of the representative strain was compared to the reference to generate variant sequences for each of the isolate. A total of 120 SNPs were used to form a genotyping panel to investigate 150 additional clinical isolates, which were characterized by both spoligotyping and MIRU. After phylogenetic analysis and the analysis for decision tree, we grouped these 156 isolates (6+150) with selected markers. To improve the genotyping panel and broaden the basis of selecting lineage-specific SNPs, we further sequenced those that could not be classified with the minimum set of SNP markers. The sequence data was then used for comparative analysis to refine the process. To obtain genome contents of representative MTB isolates from local ethnic groups and to reveal their differences with the reference strain H37Rv, we performed whole genome shotgun sequencing of six isolates using the 454 platform. Three isolates W6, M3, M7 were sequenced by the 454 GS20 sequencer with average read length of 96 base-pair. With the sequencing technique evolving, another three isolates A27, A18, M24 were sequenced by the 454 FLX sequencer with longer average read length of 227 base-pair and fewer runs of sequencing experiments. The sequencing depths were about 14X~23X in 454 GS20 data and about 16X~28X in 454 FLX data.

The mapping results were summarized in Table 3. All six isolates got at least 95.8% of mapped reads that covered 97% and above of the reference sequence. The total contig numbers for the three isolates sequenced by 454 GS20 were 214~305; while for the three isolates sequenced by 454 FLX they were 290~299. The large contig (>=1,000 bp) numbers were 134~158 for the three isolates sequenced by 454 GS20 and 196~200 for the three isolates sequenced by 454 FLX, indicating that large contigs ratio were higher for the three isolates sequenced by 454 FLX. The base quality of Phred score 40 and above (Q40Bases) for large contigs were 99.48% to 99.95% in the six isolates, indicating that the sequencing quality is high enough.

TABLE 3

Genome sequencing and mapping results of the six MTB strains

| | by 454 GS-20 | | | by 454 GS-FLX | | |
|---|---|---|---|---|---|---|
| Strain | W6 | M3 | M7 | A27 | A18 | M24 |
| Genogroup | modern-Beijing | Haarlem | LAM | T1 | EAI | ancient-Beijing |
| totalReads | 899,895 | 1,031,636 | 633,450 | 402,374 | 308,213 | 539,007 |
| totalBases | 82,327,348 | 102,358,252 | 61,414,854 | 89,801,813 | 69,425,047 | 124,997,399 |
| averageLength | 91 | 99 | 97 | 223 | 225 | 232 |
| depth (X)$^S$ | 18.66 | 23.20 | 13.92 | 20.36 | 15.74 | 28.33 |
| mappedReads | 846,966 | 1,008,774 | 605,942 | 398,267 | 304,958 | 534,763 |
| mappedBases | 78,871,442 | 100,531,219 | 59,595,662 | 88,888,588 | 68,313,195 | 123,615,730 |
| mappedRate (%) | 95.80% | 98.22% | 97.04% | 98.98% | 98.40% | 98.89% |
| totalContigs | 214 | 267 | 305 | 290 | 290 | 299 |
| totalContigLength | 4,301,167 | 4,312,708 | 4,305,621 | 4,286,613 | 4,277,247 | 4,256,888 |
| coverage (%) | 98.19% | 98.09% | 97.98% | 97.56% | 97.40% | 97.43% |
| largeContigs* | 134 | 147 | 158 | 200 | 196 | 196 |
| LargeContigLength | 4,271,545 | 4,271,928 | 4,259,176 | 4,254,158 | 4,242,400 | 4,224,733 |
| avgContigSize | 31,877 | 29,061 | 26,957 | 21,271 | 21,645 | 21,555 |
| N50ContigSize | 64,025 | 43,790 | 52,882 | 37,667 | 37,913 | 39,642 |
| largestContig | 161,689 | 132,141 | 151,052 | 151,199 | 101,590 | 129,955 |
| Q40Bases (%) | 99.75% | 99.95% | 99.59% | 99.54% | 99.48% | 99.68% |

$^S$depth = totalBases/length of H37Rv genome

*largeContig:contiglength >= 1000 bp avgContigSize & N50ContigSize are calculated from largeContigs Mapped by 454 gsMapper Release: 2.3

Genetic Variations of the MTB Clinical Isolates

We totally extracted 9,003 high-confidence (HC) variations (for the definition of HC variants, please see the Method section), including SNPs, multiple nucleotide polymorphisms (MNPs), insertions and deletions (INDELs), from the mapping results of the six isolates. After sorting these variations with reference positions, and at least one isolate with over 80% of variation frequency, there are 3,819 reference positions that all the six isolates got at least three reads covered. For simplicity, 3,582 reference positions contained only SNPs were chose for the following analysis (other 27 positions were INDELs and 210 positions were MNPs).

Among these 3,582 SNPs, 404 SNPs co-exist in all the six isolates, and 13, 19, 232, 538 SNPs exist in five, four, three, and two of the six isolates, respectively (details were shown in Table 4). The most abundant SNPs are 2,376 strain-specific (HC differences exist only in one of the six strains) and we used them as candidates for seeking lineage-specific SNPs. These candidate SNPs, according to their locations in coding or non-coding regions, are divided into three main categories: PE/PPE gene family, non-PE/PPE gene family, and intergenic SNPs (as shown in Table 2). For those SNPs in coding regions, non-synonymous SNPs seem to have more or equal number them synonymous SNPs, except in M7 isolate. And as we know that the presence of the two novel gene families PE/PPE comprises about 10% of the coding capacity of the TB genome, thus the SNPs in PE/PPE family are commonly much less than those in other non-PE/PPE gene families. A18, belongs to the EAI lineage, has 4~10 times higher numbers of specific SNPs than other five isolates, suspects that the lineage may evolve at a higher mutation rate and quickly adapt to changes in their host environment.

TABLE 4

High-confidence SNPs with total depth ≥3 and variation rate ≥80% for each site of each strain

| Comparing to the reference | # of SNPs | M3 | W6 | M7 | A18 | A27 | M24 |
|---|---|---|---|---|---|---|---|
| Differences in 1 strain | 2,376 | 133 | 270 | 317 | 1,260 | 136 | 260 |
| Differences in 2 strains | 538 | 205 | 325 | 2 | 9 | 206 | 329 |
| Differences in 3 strains | 232 | 3 | 228 | 4 | 229 | 3 | 229 |
| Differences in 4 strains | 19 | 6 | 19 | 16 | 14 | 3 | 18 |
| Differences in 5 strains | 13 | 13 | 12 | 8 | 12 | 9 | 11 |
| Differences in 6 strains | 404 | 404 | 404 | 404 | 404 | 404 | 404 |
| Sum | 3,582 | 764 | 1,258 | 751 | 1,928 | 761 | 1,251 |

SNP Genotyping on 156 M. tuberculosis Clinical Isolates

In order to characterize SNPs in 156 clinical isolates for phylogenetic analysis, 120 lineage-specific SNPs with high confidence scores were selected to design primers for Sequenom MassArray assays. These 120 lineage-specific SNPs were unequally selected from six lineage samples as shown in Table 5, which was caused by the difference in the total numbers of lineage-specific SNP between them. These 120 SNPs were divided into two categories: [5] all of 60 SNPs within PE/PPE gene family; [8] 60 of 1,215 non-synonymous SNPs within in non-PE/PPE gene family (details were shown in Table 6). Five of 120 SNPs were not designable in Sequenom matrix-assisted laser desorption inoization-time of flight mass spectrometry (MALDI-TOF) systems because of high GC contents and/or primer dimmers. 115 of 120 SNPs were designed into 10 multiplex reactions, and were genotyped in 156 clinical M. tuberculosis isolates. We excluded five SNPs with low call rate (<95%) and bad clustering pattern, and the remaining 110 SNPs are used in the following analysis. The false-positive and false-negative rates were both 0% when comparing Sequenom and 454 sequencing data, and the average call rate of each of 110 SNPs in 156 samples were 97%. There were strong correlations between these SNPs in the MTB genomes based on linkage disequilibrium analysis as shown in FIG. 2. These 110 lineage-specific SNPs were completely tagged by 25 tagSNPs with r2=1.

TABLE 5

Selection of lineage-specific SNPs for strain typing

| | Strain | | | | | |
|---|---|---|---|---|---|---|
| | M24 | W6 | A18 | M7 | M3 | A27 |
| | | | Lineage | | | |
| | ancient Beijing | modern Beijing | EAI | LAM | Haarlem | T |
| No of original lineage-specific SNPs | 260 | 270 | 1,260 | 317 | 133 | 136 |
| No of designed SNPs | 25 | 17 | 31 | 17 | 16 | 14 |
| No of actual genotyped SNPs | 22 | 17 | 29 | 15 | 15 | 12 |
| No of SNPs with 100% variant frequency in other isolates | 7 | 3 | 19 | 3 | 0 | 0 |

TABLE 6

SNP number of genotyping panel used in Sequenom MassArray

| | | Isolate (lineage) | | | | | | |
|---|---|---|---|---|---|---|---|---|
| Gene family | Substitution | M24 (ancient Beijing) | W6 (modern Beijing) | A18 (EAI) | M7 (LAM) | M3 (Haarlem) | A27 (T) | Sum |
| PE/PPE | synonymous | 5 | 1 | 5 | 4 | 3 | 2 | 60 |
| | non-synonymous | 10 | 6 | 16 | 3 | 3 | 2 | |
| non-PE/PPE | non-synonymous | 10 | 10 | 10 | 10 | 10 | 10 | 60 |
| | Sum | 25 | 17 | 31 | 17 | 16 | 14 | 120 |

Phylogenetic and Grouping Analysis of MTB Isolates

Figure 3A:
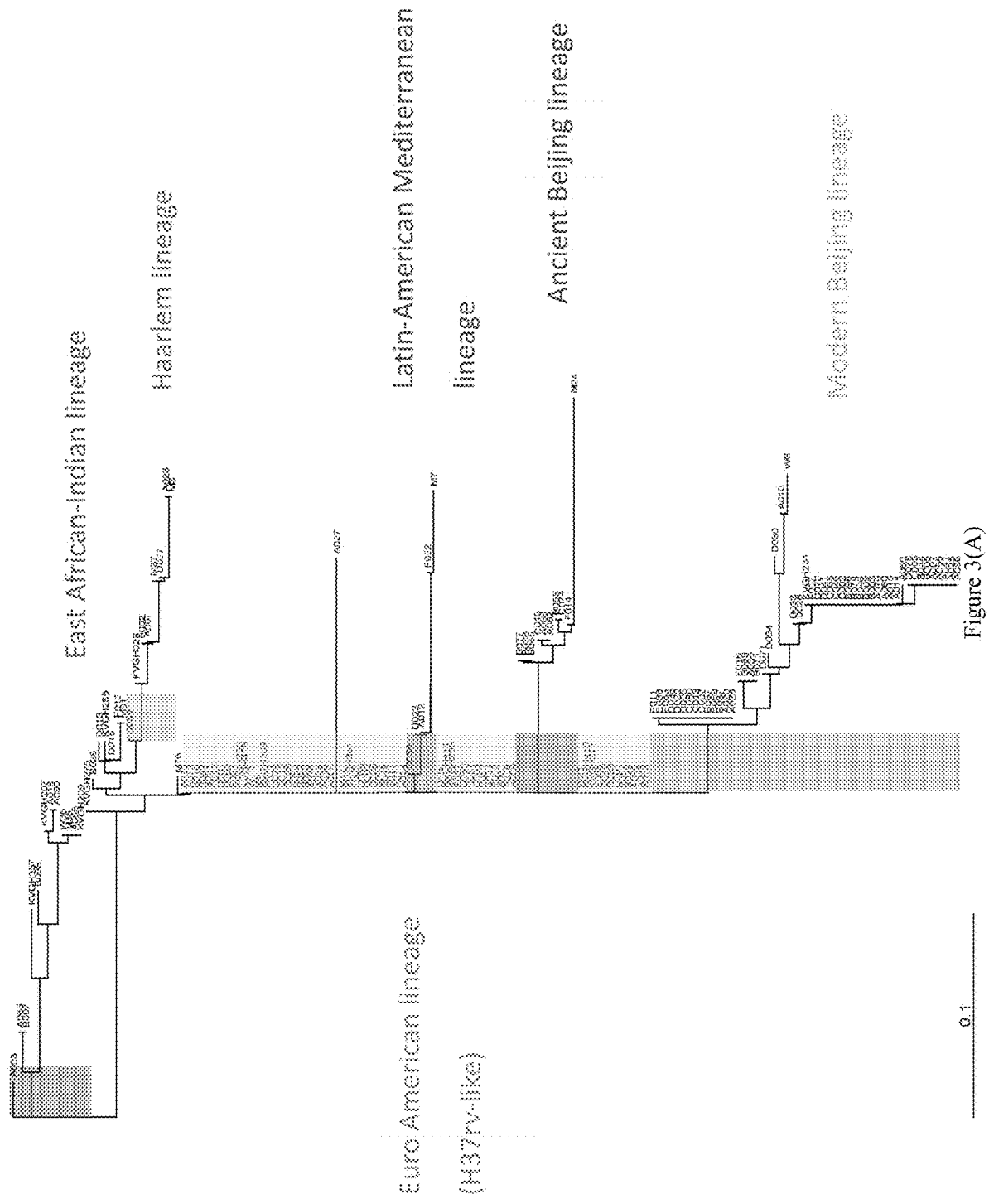
FIGS. 3(A)-3(D) illustrate phylogenetic analysis of MTB isolates using strain-specific SNP markers. Phylip software was applied to calculate the Nei's distance using 110-SNP in FIG. 3(A) and 25-tagSNP in FIG. 3(B) data, and then constructed phylogenetic trees using the neighbor joining approach, and FIGS. 3(C) and (D) illustrates typed SNP position on MTB chromosome: 110-SNP and 25-tagSNP.
Figure 3:
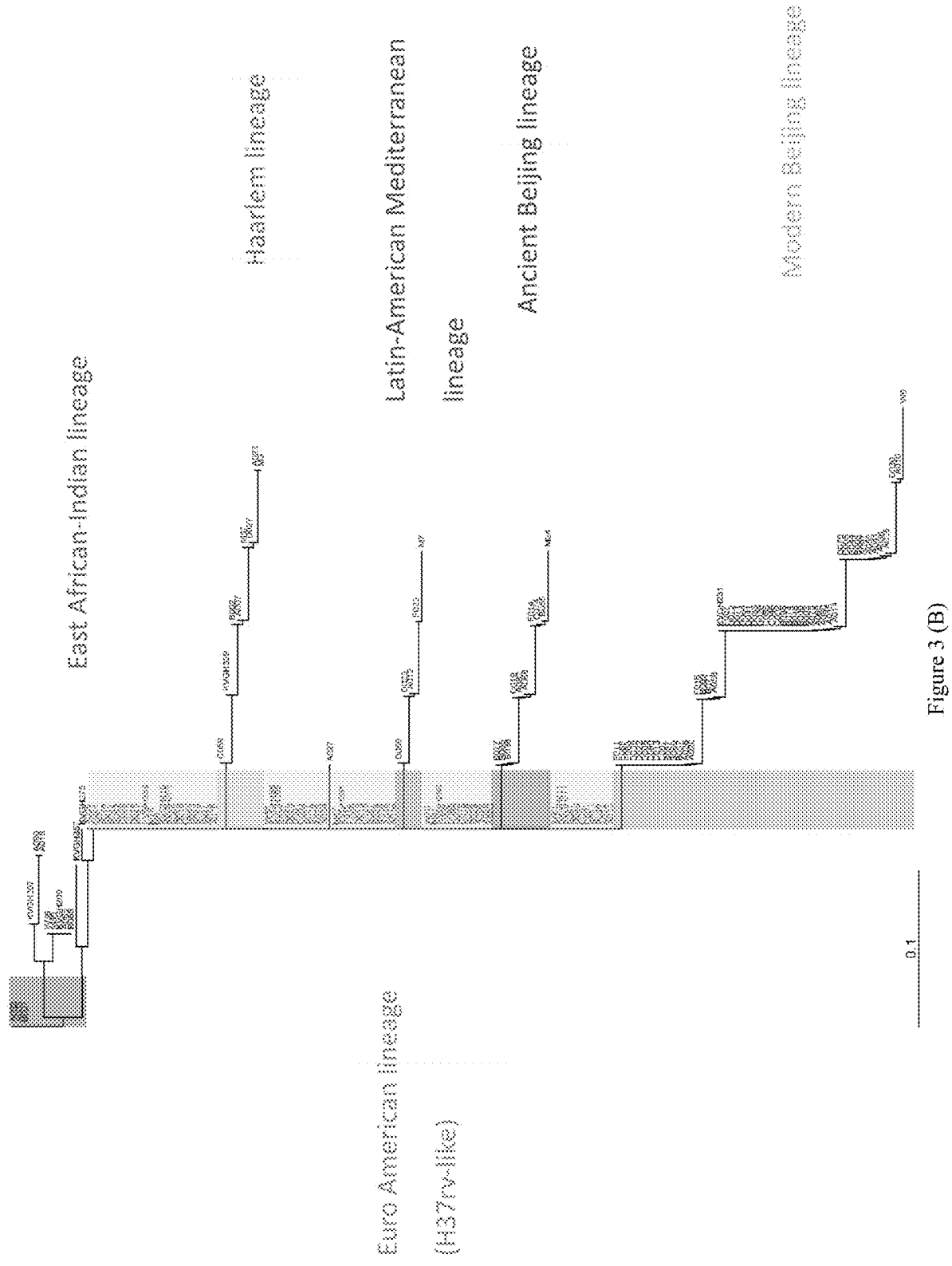
Figure 3:
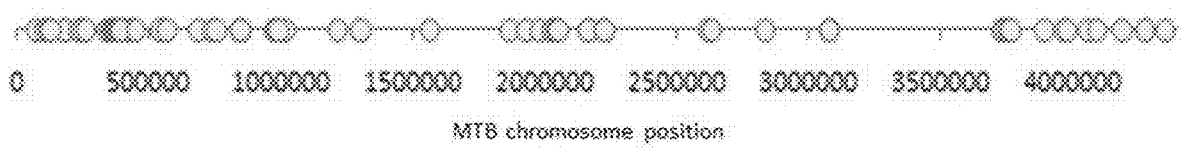
Figure 3:
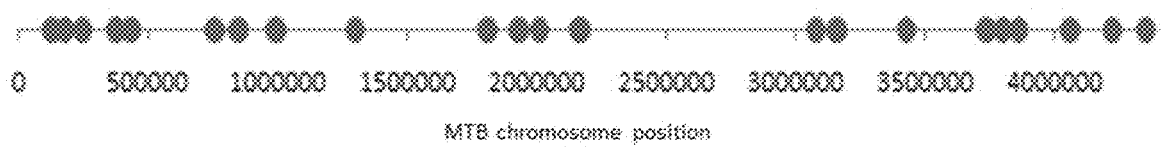

To trace the relationships between 156 clinical isolates, phylogenetic trees were constructed based on 110-SNP or 25-tagSNP information as shown in FIG. 3(A) and FIG. 3(B). The positions of 110-SNP and 25-tagSNP were shown in FIG. 3(C) and FIG. 3(D). Although the total numbers of markers used were different between these two trees, the morphology of 25-tagSNP phylogenetic tree was the same as that of 110-SNP tree, indicating that 25 tagSNPs can well represent the genomic variances between strains. Based on the preliminary lineage information from spoligotyping, 10 ancient Beijing, 51 modern Beijing, 11 EAI and 3 LAM strains were grouped into the corresponding branches in both phylogenetic trees. In addition, 6 spoligotype-unclassified isolates were suggested to belong to modern Beijing (n=2), EAI (n=2) and LAM (n=2) lineage based on the nodes of phylogenetic trees.

Figure 4:
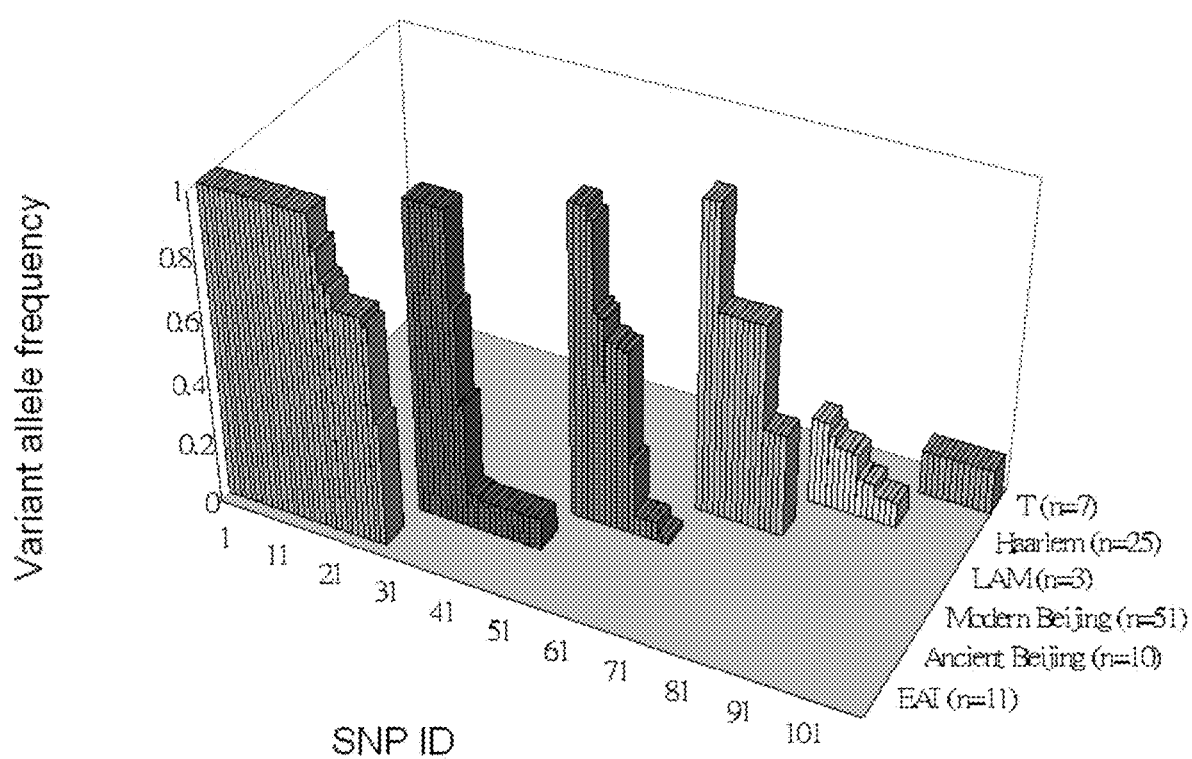
FIG. 4 shows identification of specific markers for strain typing. The allele frequencies the 110 SNPs in 51 modern Beijing, 25 Haarlem, 11 EAI, 10 ancient Beijing, 7 T and 3 LAM isolates were characterized by combining spoligotyping and SNP genotyping data.
Figure 5:
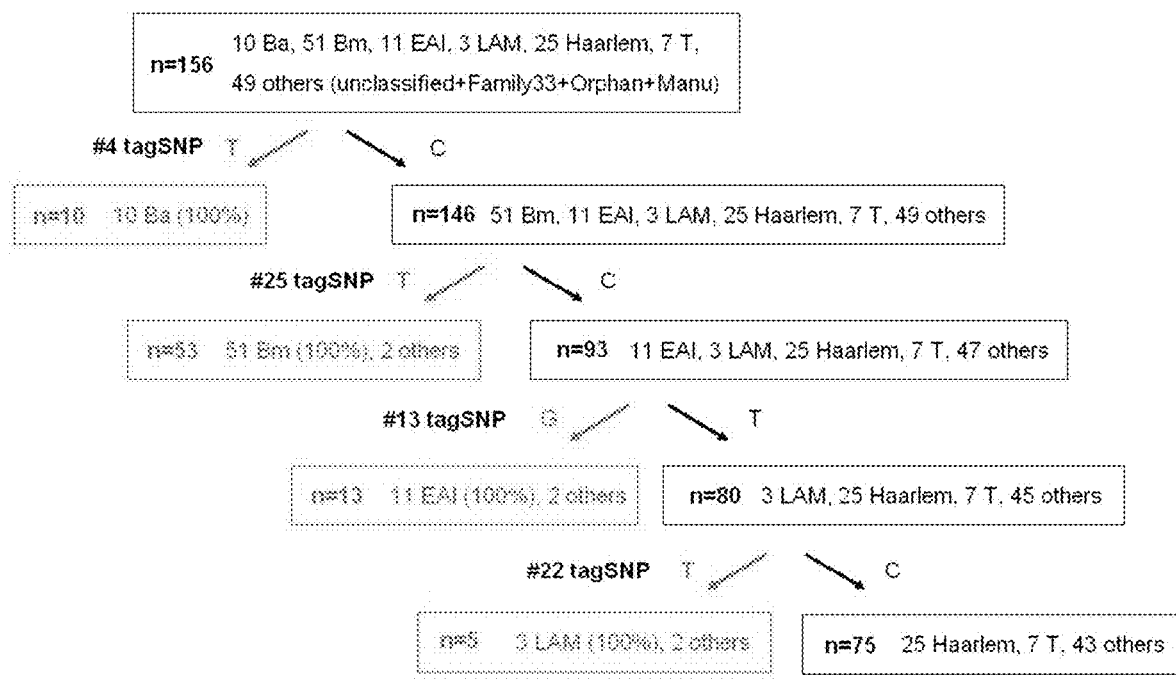
FIG. 5 illustrates decision tree based on four lineage-specific SNP markers. Four of 32 lineage-specific SNPs with 100% variant allele frequencies were used to classify 81 clinical isolates into ancient Beijing (Ba), modern Beijing (Bm), East African-Indian (EAI) and Latin American and Mediterranean (LAM) lineage.

Combination of spoligotyping and SNP genotyping data, we characterized the allele frequencies these 110 SNPs in 51 modern Beijing, 25 Haarlem, 11 EAI, 10 ancient Beijing, 7 T and 3 LAM isolates as shown in FIG. 4. All these 110 SNPs were lineage specific in these strains, and showed polymorphic in the corresponding lineage. Importantly, the variants of 32 SNPs were consensus in MTB lineage (Table 5), 7 SNPs were lineage-specific with 100% variant allele frequency in ancient Beijing, 3 in modern Beijing, 19 in EAT and 3 in LAM. Therefore, each of these 32 SNPs can be used to represent MTB lineage of ancient Beijing, modern Beijing, EAI and LAM, decision tree was constructed based on four lineage-specific SNP markers (FIG. 5). Based on the decision tree, 75 of 107 (70%) spoligotype-classified isolates can be correctly grouped into the corresponding lineage, and 6 of 49 (10.1%) spoligotype-unclassified isolates were grouped into known lineage.

Figure 6:
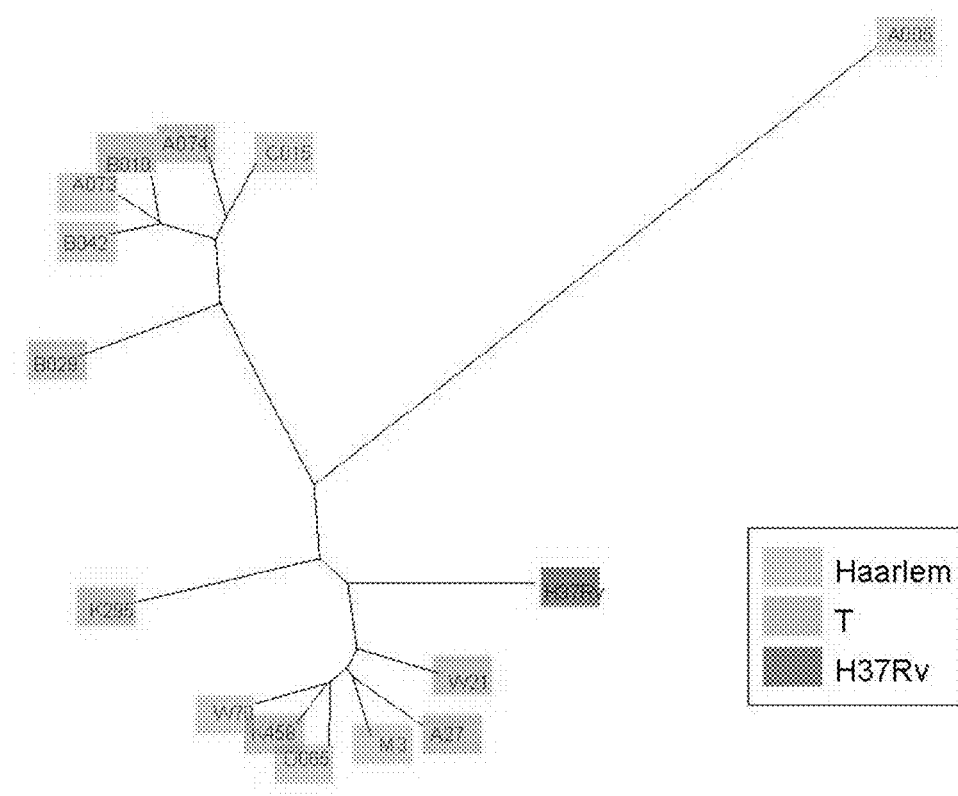
FIG. 6 shows high genetic diversity within Euro American lineage. (A) Phylogenetic analysis of Euro American strains using 4,419 whole-genome SNP markers. Phylogenetic tree was constructed based on Nei's distance using the Phylip software (neighbor joining approach). (B) Principal component analysis (PCA) of Euro American strains. The genotype data of 4,419 whole-genome SNPs was transformed into numeric values, and then PCA method was applied to analyze these 14 clinical Euro American isolates and H37Rv reference strain using SAS program.
Figure 6:
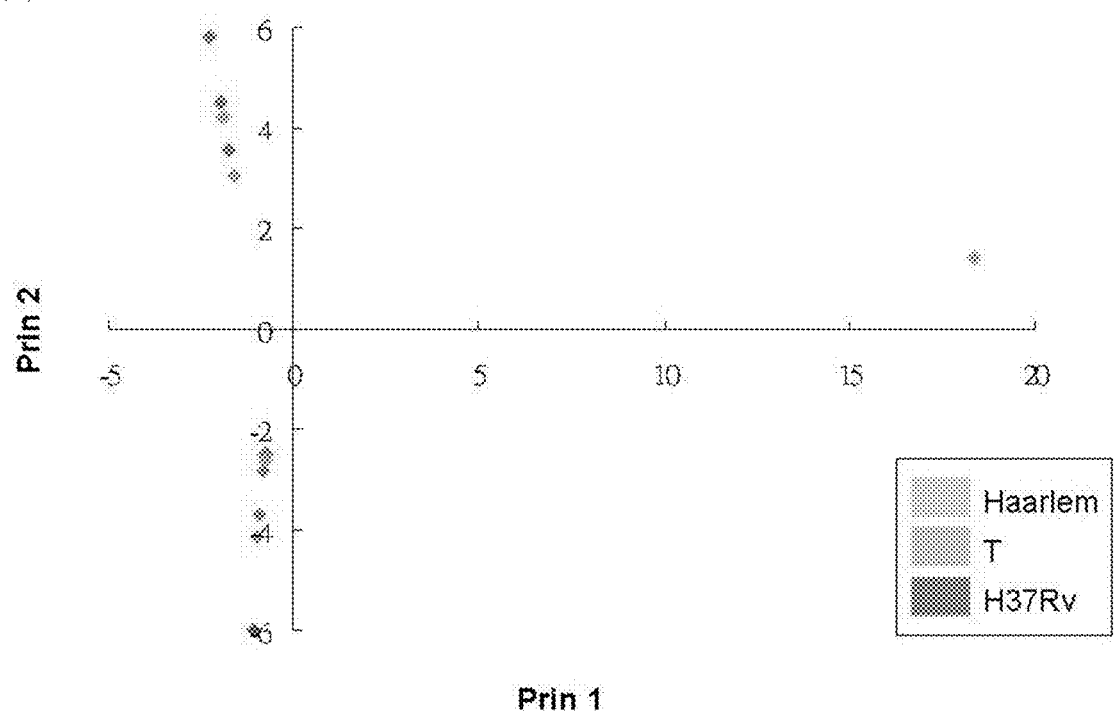
Figure 7:
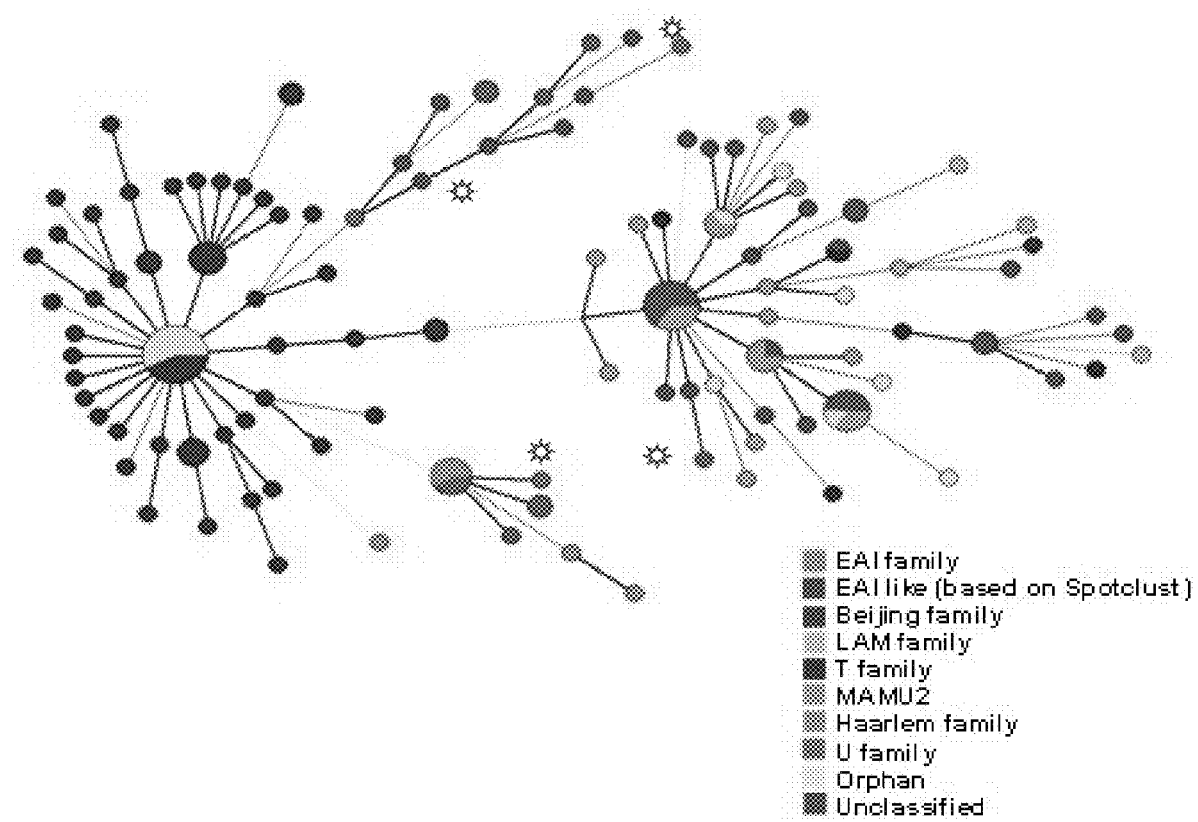
FIG. 7 shows a minimum spanning tree based on 24-MIRU-VNTR genotyping of 156 *Mycobacterium tuberculosis* isolates. The circles represent different types classified by 24-MIRU-VNTR genotypes and were colored according to the spoligotype classification. The sizes of circles represent the number of isolates with a particular genotype. (□:indicate misclassified by spoligotyping).
Figure 8:
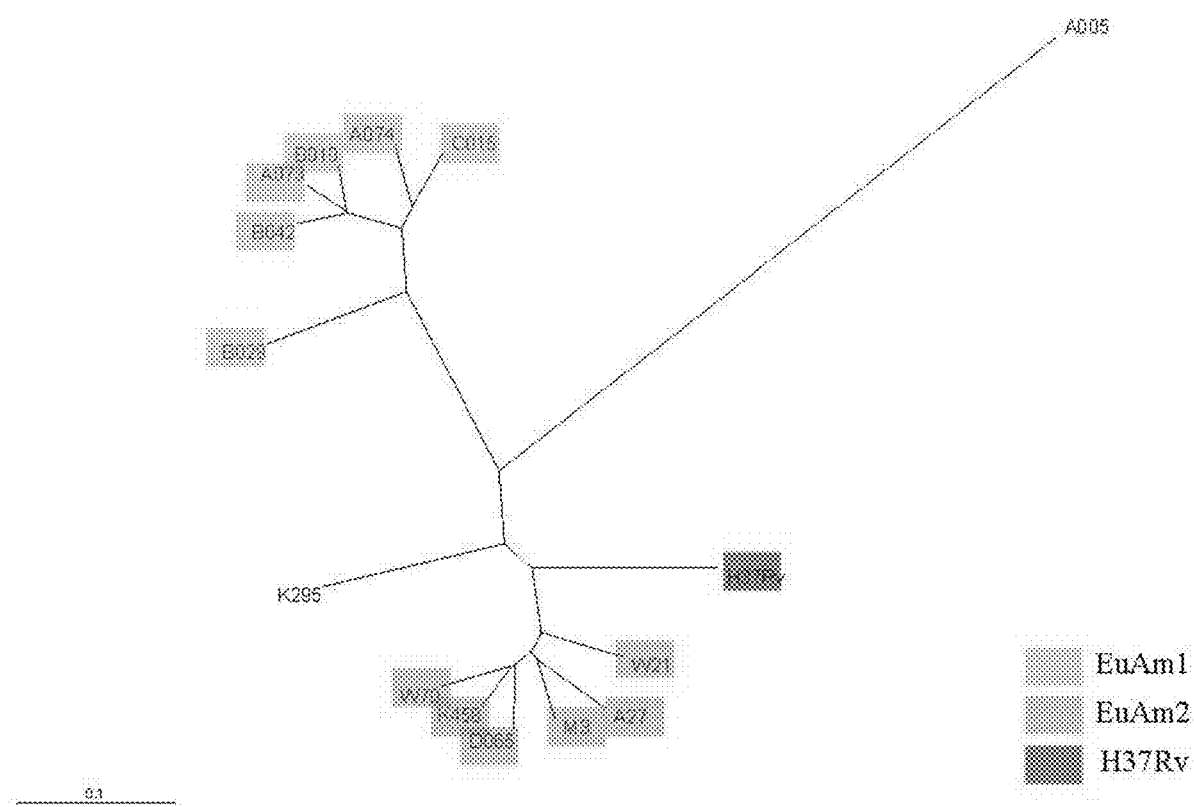
FIG. 8 shows a new hypothetic subtype definition of Euro American lineage. Phylogenetic analysis of Euro American strains using 4,419 whole-genome SNP markers. Phylogenetic tree was constructed based on Nei's distance using the Phylip software (neighbor joining approach).
Figure 9:
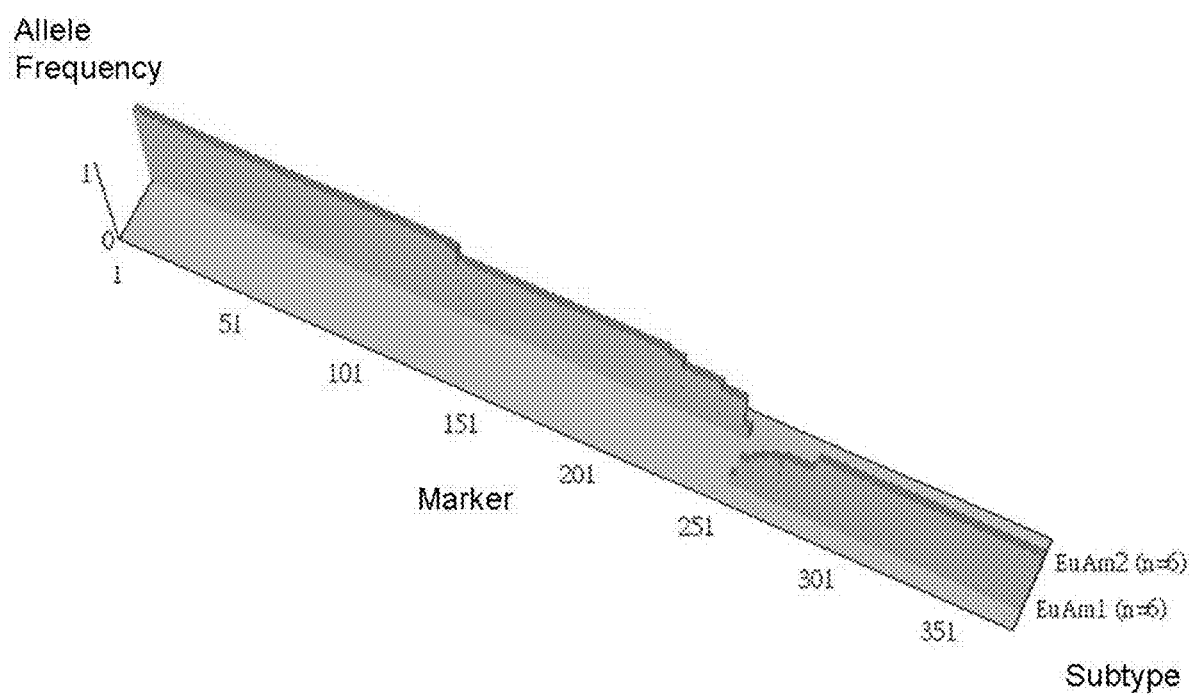
FIG. 9 shows high genetic homozygosity within new hypothetic Euro American subtypes. Fourteen Euro American strains (7 Haarlem and 7 T strains) were genome-wide sequenced using 454 or HiSe2000 sequencer, and there were two major clusters (6 and 7 belong to EuAm1 and EuAm2 subtypes, respectively) of them based on phylogenetic tree (FIG. 8). There were 81 EuAm1-specific and 133 EuAm2-specific SNPs with variant allele frequency=100%.

32 of 107 (30%) spoligotype-classified isolates were poorly classified using these 25 tagSNPs, and these isolates all belong to Euro American lineage (25 and 7 were classified as Haarlem and T strains based on spoligotype data, respectively). We hypothesized that there are high genetic heterozygosities of spoligotype-classified within Haarlem or T strains, resulting there was no leaf for Haarlem and T strains of decision tree (FIG. 5). To explore the genomic diversities of Euro American lineage, we took whole-genome sequencing to characterize genomic profiles of six Haarlem and six T strains. There were 4,419 SNPs found in these 12 Euro American strains (Table 7). We combined SNP information of M3, A27 (454 sequencing data) and these 12 samples (HiSeq2000 sequencing data) to construct phylogenetic tree and perform principal component analysis, and found the same spoligotype-classified strains were not well clustered (FIG. 6). These results demonstrated that there were high homozygosities within Euro American lineages, including Haarlem and T subtypes, and this findings was also supported by 24-MIRU-VNTR phylogenetic tree (FIG. 7). Importantly, M3 and A27 isolates, which were used to identify lineage-specific SNPs and construct decision tree (FIG. 6), were clustered together, but some Haarlem and T isolates were distant from M3 and A27, accounting for no leaf of decision tree for classifying these two subtypes. In addition, there were two major clusters of phylogenetic tree (FIG. 8), and we named these two clusters as EuAm1 and EuAm2 subtypes. Based on new proposed hypothetic definition of EuAm subtypes, there were high homozygosity within each EuAm subtype as shown in FIG. 9, and two SNPs were only needed to classify Euro American strains into two hypothetic subtypes.

TABLE 7

SNP discovery in Haarlem and T subtypes of Euro American lineage

| Data source | Isolate | Lineage | Sublinage | Total # of SNPs | PE/PPE gene family | | non-PE/PPE gene family | | Intergenic SNPs |
|---|---|---|---|---|---|---|---|---|---|
| | | | | | synonymous SNPs | non-synonymous | synonymous SNPs | non-synonymous | |
| HiSeq2000 | A005 | Haarlem | h3(st227) | 2261 | 126 | 206 | 646 | 1053 | 230 |
| | D065 | Haarlem | h3(st742) | 984 | 76 | 75 | 308 | 438 | 87 |
| | A073 | Haarlem | h3(st742) | 1651 | 107 | 154 | 460 | 744 | 186 |
| | B042 | Haarlem | st36 | 1645 | 106 | 153 | 449 | 753 | 184 |
| | C015 | Haarlem | h3(st50) | 1579 | 114 | 113 | 451 | 719 | 182 |
| | W70 | Haarlem | h3(st50) | 1009 | 65 | 71 | 351 | 435 | 87 |
| | A074 | T | T1(st102) | 1615 | 127 | 148 | 450 | 721 | 169 |
| | B010 | T | T2-T3(st73) | 1638 | 106 | 154 | 457 | 739 | 182 |
| | B029 | T | T2 (st52) | 1590 | 117 | 160 | 426 | 730 | 157 |
| | W21 | T | T1, st53 | 896 | 69 | 81 | 257 | 397 | 92 |
| | KVGH295 | T | T1 like | 1039 | 59 | 91 | 318 | 460 | 111 |
| | KVGH458 | T | T3 like | 958 | 78 | 84 | 286 | 421 | 89 |
| 454 | M3 | Haarlem | h3(st742) | 813 | 41 | 49 | 276 | 399 | 48 |
| | A27 | T | T1, st53 | 865 | 40 | 41 | 277 | 405 | 102 |

Genotyping of MTB by Using 25 tagSNPs

As described above, the 25 tagSNPs can well represent the genomic variants between strains. PCR and extension primers for 25 tagSNPs were designed using the MassArray Assay Design 3.1 software (Sequenom, San Diego, Calif.). The PCR primers, the extension primers, the positions and the correspondent alleles for the 25 tagSNPs are shown in FIG. 10. PCRs contained, in a volume of 5 ul per well, 1 pmol of the corresponding primers, 5 ng genomic DNA, and HotStar reaction Mix (Qiagen) in 384-well plates. Three wells were needed for each sample. PCR conditions were as follows: 94° C. for 15 min, followed by 40 cycles of 94° C. (20 s), 56° C. (30 s), 72° C. (60 s), and a final extension of 72° C. for 3 min. In the primer extension procedure, each sample was denatured at 94° C., followed by 40 cycles of 94° C. (5 s), 52° C. (5 s), 72° C. (5 s). The mass spectrum from time-resolved spectra was retrieved by using a MassARRAY mass spectrometer (Sequenom), and each spectrum was then analyzed using the Sequenom Typer 4.0 software (Sequenom) to perform the SNP genotype calling.

Discussion

Tuberculosis remains a major public health issue in Taiwan and throughout the world. Over the past years, the development of genotyping methods for molecular epidemiology study of tuberculosis has advanced our understanding of the transmission of MTB in human populations. Classification of strains into sub-lineages provides perspective on the phenotypic consequences of genetic variations of the MTB strains. Phylogenic analyses of MTB strains have also offered new insights regarding the evolution of MTB and the existence of distinct clades. From public health perspective, an ideal methodology to determine the genetic variation of MTB clinical isolates should be simple, affordable, have a rapid turnaround time, and the result should be transferrable in a format that can be easily shared between laboratories. In this study, we have designed a selection scheme of lineage-specific markers by genome sequencing, comparative analysis, and genotyping with DNA mass spectrometry, and also demonstrated the utility and accuracy of this new typing protocol. Because of its speed and ease of laboratory operation and the simple data format for exchange and comparison, the protocol reported here has the potential to become a new standard method. It should prove valuable for the development of an effective infection-control policy.

Although spoligotyping analysis is a straightforward technique, it is less discriminatory than IS6110 RFLP. Moreover, it is a labor-intensive and time-consuming procedure. Even through strain classification based on spoligotyping can assign MTBC strains to the correct phylogenetic lineages in about 90% of the cases, some strains cannot be classified at all, and others might be misclassified as shown in this study (FIG. 7). Analysis of MIRU-VNTR loci is reproducible and sensitive, and it provides a better resolution than spoligotyping. However, dependent on the context, such investigations can be less than or as discriminatory as IS6110 RFLP. Strain-specific SNP typing can provide precise sequence-based information, and could be automated for large-scale studies of molecular epidemiology and phylogenetics. The combination of spoligotyping and MIRU-typing can be considered a cost-effective method for TB genotyping. However, the spoligotype is still only about 20-40% strains that cannot be sorted, and nothing in this law to compensate for this shortcoming. The proposed MIRU-VNTR typing method could not sufficiently differentiate M. tuberculosis strains comprising many Beijing genotype strains. Therefore, this typing method could not be used for routine epidemiological study in areas where the Beijing genotype is prevalent. The addition of several VNTR loci is required to use VNTR typing as a routine epidemiological tool without doing RFLP analysis.

Additional genotyping of M. tuberculosis isolates is essential for understanding the dynamics of transmission. Genetic information will help determine precise quantitative measures for transmission dynamics and augment classical epidemiological models. The ability to assess the inter-strain genetic relationships provides a powerful means of resolving a number of epidemiological issues, such as tracing of chains of transmission, determining sources of infection, differentiating recent transmission from reactivation and reinfection from relapse or treatment failure, detecting laboratory cross-contaminations, monitoring the geographic distribution and spread of particular genetic strains (including those of special epidemiological importance), or investigating the evolution of M. tuberculosis.

The proposed workflow of selecting lineage-specific DNA marker (FIG. 1) is an effective and logistical way to discriminate MTB isolates into genetic subtypes. Importantly, the concept of our workflow is also applicable in other fields of microbial projects, e.g., searching highly conserved domains of variable clinical isolates for vaccine development.

FIG. 11 shows the comparisons of the present application and the conventional genotyping methods. For the 25 tag-SNPs genotyping method of the present application, the sample needed for the detection is as low as 20 ng of DNA sample for PCR. Based on the MALDI-TOF technology, the specificity and the sensitivity of sequence detection is able to achieve almost 100%, but conventional PCR-based spoligotyping and MIRU cannot. By using 25 tagSNPs genotyping method of the present application, detection of 192 samples can be completed within 48 hours. Accordingly, advantages of the 25 tagSNPs genotyping method described herein include excellent specificity and sensitivity, less sample requirements, rapid and large scale detection.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims and its equivalent systems and methods.

What is claimed is:

1. A method for genotyping *Mycobacterium tuberculosis*, comprising the steps of:
obtaining a DNA from a sample,
amplifying and obtaining at least one first DNA fragment by using the obtained DNA as template and a combination of primer sets comprising Primer set 4: ACGTTGGATGATCGGACAGCAGAAGGCAC (SEQ ID No: 7) and ACGTTGGATGACTCCCGCGGAACGTGGTG (SEQ ID No: 8), Primer set 13: ACGTTGGATGTGCTACCGCCAATGTTCAAC (SEQ ID No: 25) and ACGTTGGATGATGGCGTTGACATAACTCGG (SEQ ID No: 26), Primer set 22: ACGTTGGATGAGCGTGAAGAAGACGACGA (SEQ ID No: 43) and ACGTTGGATGGTCTGTTGTCATTACGGGAG (SEQ ID No: 44), and Primer set 25: ACGTTGGATGTCTTGGCAGCGGCATGGAC (SEQ ID No: 49) and ACGTTGGATGCCGAATTTCCAGTCTCACAG (SEQ ID No: 50);
amplifying and obtaining at least one second DNA fragment having a single-nucleotide polymorphism (SNP) of *M. tuberculosis* as a terminal nucleotide of the DNA fragment by using the obtained at least one first DNA fragment as template and a combination of extension primers comprising CCCCCGACCGGCCGTTCTTCG (SEQ ID No: 54), CAAAATACGGCGATCATCATGGG (SEQ ID No: 63), GAAGACGACGAGGACGACTGGG (SEQ ID No: 72) and GGCATGGACGGGATCGG (SEQ ID No: 75); and
detecting the at least one second DNA fragment by using mass spectrometry.

2. The method of claim 1, further comprising analyzing the mass spectrometry data based on a combination of single-nucleotide polymorphism markers of *M. tuberculosis* consisting of "T" at position 301 of SEQ ID No: 76, "A" at position 301 of SEQ ID No: 77, "A" at position 301 of SEQ ID No: 78, "G" at position 301 of SEQ ID No: 79, "G" at position 301 of SEQ ID No: 80, "G" at position 301 of SEQ ID No: 81, "C" at position 301 of SEQ ID No: 82, "G" at position 301 of SEQ ID No: 83, "C" at position 301 of SEQ ID No: 84, "A" at position 301 of SEQ ID No: 85, "A" at position 301 of SEQ ID No: 86, "A" at position 301 of SEQ ID No: 87, "G" at position 301 of SEQ ID No: 88, "A" at position 301 of SEQ ID No: 89, "G" at position 301 of SEQ ID No: 90, "G" at position 301 of SEQ ID No: 91, "A" at position 301 of SEQ ID No: 92, "C" at position 301 of SEQ ID No: 93, "C" at position 301 of SEQ ID No: 94, "T" at position 301 of SEQ ID No: 95, "T" at position 301 of SEQ ID No: 96, "T" at position 301 of SEQ ID No: 97, "T" at position 301 of SEQ ID No: 98, "T" at position 301 of SEQ ID No: 99, and "C" at position 301 of SEQ ID No: 100.

3. The method of claim 1, wherein the mass spectrometry is matrix-assisted laser desorption ionization time-of-flight mass spectrometry (MALDI-TOF MS).

4. The method of claim 1, wherein the sample is a bacterial culture, nasal mucus, phlegm, saliva, blood, a section of tissues, organs or a biopsy.

5. The method of claim 1, wherein the combination of primer sets further comprises one or more primer sets selected from the group consisting of:

```
Primer set 1:
                                    (SEQ ID No. 1)
ACGTTGGATGTTCTGGACGACCTGTCCTAC
and
                                    (SEQ ID No. 2)
ACGTTGGATGAGCTGCGCCAAGGTTCGTG, Primer set 2:
                                    (SEQ ID No. 3)
ACGTTGGATGTTGTAGCTGCCCAAATTGCC
and
                                    (SEQ ID No. 4)
ACGTTGGATGGGCTTCAATCTCGGCTTGG, Primer set 3:
                                    (SEQ ID No. 5)
ACGTTGGATGTATTCAACACCGGCATCGGG
and
                                    (SEQ ID No. 6)
ACGTTGGATGTCGCCTGGTCGTGGAAGAAC, Primer set 5:
                                    (SEQ ID No. 9)
ACGTTGGATGCAACACCGGCAACTTCAAC
and
                                    (SEQ ID No. 10)
ACGTTGGATGAATTAGCGTCTCCTCCGTTG, Primer set 6:
                                    (SEQ ID No. 11)
ACGTTGGATGTCGAACCCGCCGACAAATG
and
                                    (SEQ ID No. 12)
ACGTTGGATGTCGATTGGTCGCATGCACTG,
```

-continued

Primer set 7:
(SEQ ID No. 13)
ACGTTGGATGAAACCTCGGCATAGGGATCG (SEQ ID No. 14)
ACGTTGGATGTCGACAGGACTATTGGTAGC,
and Primer set 8:
(SEQ ID No. 15)
ACGTTGGATGAAGACGACGGGCCGGATATG
and (SEQ ID No. 16)
ACGTTGGATGCGTCAAGAGCTTCCCAAATC, Primer set 9:
(SEQ ID No. 17)
ACGTTGGATGCATCCGGGAACACCGTAAAC
and (SEQ ID No. 18)
ACGTTGGATGATCACCTTCTTATCGGGTGG, Primer set 10:
(SEQ ID No. 19)
ACGTTGGATGCCTGGATTTCAGATATTGCC
and (SEQ ID No. 20)
ACGTTGGATGTGGCCAGCCCTAGCAAGTC, Primer set 11:
(SEQ ID No. 21)
ACGTTGGATGAGAACAAACGCGGGATTCAC
and (SEQ ID No. 22)
ACGTTGGATGTCTCCCGGAGATCACCATTC, Primer set 12:
(SEQ ID No. 23)
ACGTTGGATGGTTGTTTTGGCCGGGCAG
and (SEQ ID No. 24)
ACGTTGGATGATCGAGCAGACTCAGCGCTT, Primer set 14:
(SEQ ID No. 27)
ACGTTGGATGATAGCAAGCACGATTGCGAC
and (SEQ ID No. 28)
ACGTTGGATGACCCCCCGCTGAGGGCGTA, Primer set 15:
(SEQ ID No. 29)
ACGTTGGATGGATTCGATTGGGGAAACGGC
and (SEQ ID No. 30)
ACGTTGGATGTTCCACATTGGTGATCAGCG, Primer set 16:
(SEQ ID No. 31)
ACGTTGGATGCAAACGGCGTCACTTTGGTC
and (SEQ ID No. 32)
ACGTTGGATGTGAAATGTGGGCCCAAGACG, Primer set 17:
(SEQ ID No. 33)
ACGTTGGATGCGATTTCGATCGGGATGTTG
and (SEQ ID No. 34)
ACGTTGGATGCAATCACGATCCCCTCAATC, -continued Primer set 18:
(SEQ ID No. 35)
ACGTTGGATGAGGCAAAGGAAAATCGACCG
and (SEQ ID No. 36)
ACGTTGGATGTTGACAAACTGAAACACCGC, Primer set 19:
(SEQ ID No. 37)
ACGTTGGATGACAACCGGCCGCAGCGTTT
and (SEQ ID No. 38)
ACGTTGGATGAAGAACACCGAAAGTGGCTG, Primer set 20:
(SEQ ID No. 39)
ACGTTGGATGTGCATTGGCCACTAAAGCTC
and (SEQ ID No. 40)
ACGTTGGATGTCGATGACTATCTGCGGATG, Primer set 21:
(SEQ ID No. 41)
ACGTTGGATGACCCATTTGCCGAACGTGTC
and (SEQ ID No. 42)
ACGTTGGATGTGCTTGGCGACTTTGTGCAG, Primer set 23:
(SEQ ID No. 45)
ACGTTGGATGACATCAGGTGATGGTCATGC
and (SEQ ID No. 46)
ACGTTGGATGCGAAGGGAACAATGGATGTG,
and Primer set 24:
(SEQ ID No. 47)
ACGTTGGATGTATGCCAACCGATTTGCCTG
and (SEQ ID No. 48)
ACGTTGGATGACATATTGTCCACCGCGTAG.

6. The method of claim 5, wherein the combination of extension primers further comprises one or more extension primers selected from one of the group consisting of:

(SEQ ID No. 51)
GACCTGTCCTACGAACCGGTGATGG, (SEQ ID No. 52)
CGTTGCCCACGTTGTTGGCG, (SEQ ID No. 53)
CACCGGCCAACGTCTCGGGCATG, (SEQ ID No. 55)
TTCAACGGCGGCATCAT, (SEQ ID No. 56)
GCCGAAACAAGATTTGC, (SEQ ID No. 57)
CCTTCTGCGTCTCCAAT, (SEQ ID No. 58)
GATATGGGGCCGCGGAT, (SEQ ID No. 59)
ACCGTAAACGGGCCTAACCCTCC, (SEQ ID No. 60)
TTGGGGCTGGGAACTGGG,

-continued

ATTCACGTGAAAACCCTCG,, (SEQ ID No. 61)

AGCTCAGCGCGCGGCTGGTGT, (SEQ ID No. 62)

CCACCAGTACTTGCCGC, (SEQ ID No. 64)

ATCGGGGTGACGATGAG, (SEQ ID No. 65)

GCCGAGGAGCCCGCGTAACCGT, (SEQ ID No. 66)

TGTTGATCGGCCCGAGGC, (SEQ ID No. 67)

GCGGGCGTGGAACGCTGGTC, (SEQ ID No. 68)

AGCGTTTCCAGGTCCCGCA, (SEQ ID No. 69)

CCAGAGCGCAACAACAA, (SEQ ID No. 70)

CACGCTGGCATCAAGTTC,, (SEQ ID No. 71)

GACGATTCCGGGCATGCG,
and (SEQ ID No. 73)

TGCCTGCCTGGTATGAC. (SEQ ID No. 74)

\* \* \* \* \*

SEQUENCE LISTING

```
<160> NUMBER OF SEQ ID NOS: 100

<210> SEQ ID NO 1
<211> LENGTH: 30
<212> TYPE: DNA
<213> ORGANISM: Artificial Sequence
<220> FEATURE:
<223> OTHER INFORMATION: Primer set 1_Forward primer
<220> FEATURE:
<221> NAME/KEY: misc_feature
<223> OTHER INFORMATION: Forward primer

<400> SEQUENCE: 1
acgttggatg ttctggacga cctgtcctac                                        30

<210> SEQ ID NO 2
<211> LENGTH: 29
<212> TYPE: DNA
<213> ORGANISM: Artificial Sequence
<220> FEATURE:
<223> OTHER INFORMATION: Primer set 1_Reverse primer
<220> FEATURE:
<221> NAME/KEY: misc_feature
<223> OTHER INFORMATION: Reverse primer

<400> SEQUENCE: 2
acgttggatg agctgcgcca aggttcgtg                                         29

<210> SEQ ID NO 3
<211> LENGTH: 30
<212> TYPE: DNA
<213> ORGANISM: Artificial Sequence
<220> FEATURE:
<223> OTHER INFORMATION: Primer set 2_Forward primer
<220> FEATURE:
<221> NAME/KEY: misc_feature
<223> OTHER INFORMATION: Forward primer

<400> SEQUENCE: 3
acgttggatg ttgtagctgc ccaaattgcc                                        30

<210> SEQ ID NO 4
<211> LENGTH: 29
<212> TYPE: DNA
<213> ORGANISM: Artificial Sequence
<220> FEATURE:
<223> OTHER INFORMATION: Primer set 2_Reverse primer
<220> FEATURE:
<221> NAME/KEY: misc_feature
<223> OTHER INFORMATION: Reverse primer

<400> SEQUENCE: 4
acgttggatg ggcttcaatc tcggcttgg                                         29
```

-continued

```
<210> SEQ ID NO 5
<211> LENGTH: 30
<212> TYPE: DNA
<213> ORGANISM: Artificial Sequence
<220> FEATURE:
<223> OTHER INFORMATION: Primer set 3_Forward primer
<220> FEATURE:
<221> NAME/KEY: misc_feature
<223> OTHER INFORMATION: Forward primer

<400> SEQUENCE: 5
acgttggatg tattcaacac cggcatcggg                                        30

<210> SEQ ID NO 6
<211> LENGTH: 30
<212> TYPE: DNA
<213> ORGANISM: Artificial Sequence
<220> FEATURE:
<223> OTHER INFORMATION: Primer set 3_Reverse primer
<220> FEATURE:
<221> NAME/KEY: misc_feature
<223> OTHER INFORMATION: Reverse primer

<400> SEQUENCE: 6
acgttggatg tcgcctggtc gtggaagaac                                        30

<210> SEQ ID NO 7
<211> LENGTH: 29
<212> TYPE: DNA
<213> ORGANISM: Artificial Sequence
<220> FEATURE:
<223> OTHER INFORMATION: Primer set 4_Forward primer
<220> FEATURE:
<221> NAME/KEY: misc_feature
<223> OTHER INFORMATION: Forward primer

<400> SEQUENCE: 7
acgttggatg atcggacagc agaaggcac                                         29

<210> SEQ ID NO 8
<211> LENGTH: 29
<212> TYPE: DNA
<213> ORGANISM: Artificial Sequence
<220> FEATURE:
<223> OTHER INFORMATION: Primer set 4_Reverse primer
<220> FEATURE:
<221> NAME/KEY: misc_feature
<223> OTHER INFORMATION: Reverse primer

<400> SEQUENCE: 8
acgttggatg actcccgcgg aacgtggtg                                         29

<210> SEQ ID NO 9
<211> LENGTH: 29
<212> TYPE: DNA
<213> ORGANISM: Artificial Sequence
<220> FEATURE:
<223> OTHER INFORMATION: Primer set 5_Forward primer
<220> FEATURE:
<221> NAME/KEY: misc_feature
<223> OTHER INFORMATION: Forward primer

<400> SEQUENCE: 9
acgttggatg caacaccggc aacttcaac                                         29

<210> SEQ ID NO 10
<211> LENGTH: 30
<212> TYPE: DNA
```

```
<213> ORGANISM: Artificial Sequence
<220> FEATURE:
<223> OTHER INFORMATION: Primer set 5_Reverse primer
<220> FEATURE:
<221> NAME/KEY: misc_feature
<223> OTHER INFORMATION: Reverse primer

<400> SEQUENCE: 10
acgttggatg aattagcgtc tcctccgttg                                    30

<210> SEQ ID NO 11
<211> LENGTH: 29
<212> TYPE: DNA
<213> ORGANISM: Artificial Sequence
<220> FEATURE:
<223> OTHER INFORMATION: Primer set 6_Forward primer
<220> FEATURE:
<221> NAME/KEY: misc_feature
<223> OTHER INFORMATION: Forward primer

<400> SEQUENCE: 11
acgttggatg tcgaacccgc cgacaaatg                                     29

<210> SEQ ID NO 12
<211> LENGTH: 30
<212> TYPE: DNA
<213> ORGANISM: Artificial Sequence
<220> FEATURE:
<223> OTHER INFORMATION: Primer set 6_Reverse primer
<220> FEATURE:
<221> NAME/KEY: misc_feature
<223> OTHER INFORMATION: Reverse primer

<400> SEQUENCE: 12
acgttggatg tcgattggtc gcatgcactg                                    30

<210> SEQ ID NO 13
<211> LENGTH: 30
<212> TYPE: DNA
<213> ORGANISM: Artificial Sequence
<220> FEATURE:
<223> OTHER INFORMATION: Primer set 7_Forward primer
<220> FEATURE:
<221> NAME/KEY: misc_feature
<223> OTHER INFORMATION: Forward primer

<400> SEQUENCE: 13
acgttggatg aaacctcggc atagggatcg                                    30

<210> SEQ ID NO 14
<211> LENGTH: 30
<212> TYPE: DNA
<213> ORGANISM: Artificial Sequence
<220> FEATURE:
<223> OTHER INFORMATION: Primer set 7_Reverse primer
<220> FEATURE:
<221> NAME/KEY: misc_feature
<223> OTHER INFORMATION: Reverse primer

<400> SEQUENCE: 14
acgttggatg tcgacaggac tattggtagc                                    30

<210> SEQ ID NO 15
<211> LENGTH: 30
<212> TYPE: DNA
<213> ORGANISM: Artificial Sequence
<220> FEATURE:
<223> OTHER INFORMATION: Primer set 8_Forward primer
<220> FEATURE:
```

```
<221> NAME/KEY: misc_feature
<223> OTHER INFORMATION: Forward primer

<400> SEQUENCE: 15
acgttggatg aagacgacgg gccggatatg                                    30

<210> SEQ ID NO 16
<211> LENGTH: 30
<212> TYPE: DNA
<213> ORGANISM: Artificial Sequence
<220> FEATURE:
<223> OTHER INFORMATION: Primer set 8_Reverse primer
<220> FEATURE:
<221> NAME/KEY: misc_feature
<223> OTHER INFORMATION: Reverse primer

<400> SEQUENCE: 16
acgttggatg cgtcaagagc ttcccaaatc                                    30

<210> SEQ ID NO 17
<211> LENGTH: 30
<212> TYPE: DNA
<213> ORGANISM: Artificial Sequence
<220> FEATURE:
<223> OTHER INFORMATION: Primer set 9_Forward primer
<220> FEATURE:
<221> NAME/KEY: misc_feature
<223> OTHER INFORMATION: Forward primer

<400> SEQUENCE: 17
acgttggatg catccgggaa caccgtaaac                                    30

<210> SEQ ID NO 18
<211> LENGTH: 30
<212> TYPE: DNA
<213> ORGANISM: Artificial Sequence
<220> FEATURE:
<223> OTHER INFORMATION: Primer set 9_Reverse primer
<220> FEATURE:
<221> NAME/KEY: misc_feature
<223> OTHER INFORMATION: Reverse primer

<400> SEQUENCE: 18
acgttggatg atcaccttct tatcgggtgg                                    30

<210> SEQ ID NO 19
<211> LENGTH: 30
<212> TYPE: DNA
<213> ORGANISM: Artificial Sequence
<220> FEATURE:
<223> OTHER INFORMATION: Primer set 10_Forward primer
<220> FEATURE:
<221> NAME/KEY: misc_feature
<223> OTHER INFORMATION: Forward primer

<400> SEQUENCE: 19
acgttggatg cctggatttc agatattgcc                                    30

<210> SEQ ID NO 20
<211> LENGTH: 29
<212> TYPE: DNA
<213> ORGANISM: Artificial Sequence
<220> FEATURE:
<223> OTHER INFORMATION: Primer set 10_Reverse primer
<220> FEATURE:
<221> NAME/KEY: misc_feature
<223> OTHER INFORMATION: Reverse primer

<400> SEQUENCE: 20
```
acgttggatg tggccagccc tagcaagtc                                              29

<210> SEQ ID NO 21
<211> LENGTH: 30
<212> TYPE: DNA
<213> ORGANISM: Artificial Sequence
<220> FEATURE:
<223> OTHER INFORMATION: Primer set 11_Forward primer
<220> FEATURE:
<221> NAME/KEY: misc_feature
<223> OTHER INFORMATION: Forward primer

<400> SEQUENCE: 21
acgttggatg agaacaaacg cgggattcac                                             30

<210> SEQ ID NO 22
<211> LENGTH: 30
<212> TYPE: DNA
<213> ORGANISM: Artificial Sequence
<220> FEATURE:
<223> OTHER INFORMATION: Primer set 11_Reverse primer
<220> FEATURE:
<221> NAME/KEY: misc_feature
<223> OTHER INFORMATION: Reverse primer

<400> SEQUENCE: 22
acgttggatg tctcccggag atcaccattc                                             30

<210> SEQ ID NO 23
<211> LENGTH: 29
<212> TYPE: DNA
<213> ORGANISM: Artificial Sequence
<220> FEATURE:
<223> OTHER INFORMATION: Primer set 12_Forward primer
<220> FEATURE:
<221> NAME/KEY: misc_feature
<223> OTHER INFORMATION: Forward primer

<400> SEQUENCE: 23
acgttggatg gttgtttttg gccgggcag                                              29

<210> SEQ ID NO 24
<211> LENGTH: 30
<212> TYPE: DNA
<213> ORGANISM: Artificial Sequence
<220> FEATURE:
<223> OTHER INFORMATION: Primer set 12_Reverse primer
<220> FEATURE:
<221> NAME/KEY: misc_feature
<223> OTHER INFORMATION: Reverse primer

<400> SEQUENCE: 24
acgttggatg atcgagcaga ctcagcgctt                                             30

<210> SEQ ID NO 25
<211> LENGTH: 30
<212> TYPE: DNA
<213> ORGANISM: Artificial Sequence
<220> FEATURE:
<223> OTHER INFORMATION: Primer set 13_Forward primer
<220> FEATURE:
<221> NAME/KEY: misc_feature
<223> OTHER INFORMATION: Forward primer

<400> SEQUENCE: 25
acgttggatg tgctaccgcc aatgttcaac                                             30

```
<210> SEQ ID NO 26
<211> LENGTH: 30
<212> TYPE: DNA
<213> ORGANISM: Artificial Sequence
<220> FEATURE:
<223> OTHER INFORMATION: Primer set 13_Reverse primer
<220> FEATURE:
<221> NAME/KEY: misc_feature
<223> OTHER INFORMATION: Reverse primer

<400> SEQUENCE: 26
acgttggatg atggcgttga cataactcgg                                    30

<210> SEQ ID NO 27
<211> LENGTH: 30
<212> TYPE: DNA
<213> ORGANISM: Artificial Sequence
<220> FEATURE:
<223> OTHER INFORMATION: Primer set 14_Forward primer
<220> FEATURE:
<221> NAME/KEY: misc_feature
<223> OTHER INFORMATION: Forward primer

<400> SEQUENCE: 27
acgttggatg atagcaagca cgattgcgac                                    30

<210> SEQ ID NO 28
<211> LENGTH: 29
<212> TYPE: DNA
<213> ORGANISM: Artificial Sequence
<220> FEATURE:
<223> OTHER INFORMATION: Primer set 14_Reverse primer
<220> FEATURE:
<221> NAME/KEY: misc_feature
<223> OTHER INFORMATION: Reverse primer

<400> SEQUENCE: 28
acgttggatg acccccgct gagggcgta                                      29

<210> SEQ ID NO 29
<211> LENGTH: 30
<212> TYPE: DNA
<213> ORGANISM: Artificial Sequence
<220> FEATURE:
<223> OTHER INFORMATION: Primer set 15_Forward primer
<220> FEATURE:
<221> NAME/KEY: misc_feature
<223> OTHER INFORMATION: Forward primer

<400> SEQUENCE: 29
acgttggatg gattcgattg gggaaacggc                                    30

<210> SEQ ID NO 30
<211> LENGTH: 30
<212> TYPE: DNA
<213> ORGANISM: Artificial Sequence
<220> FEATURE:
<223> OTHER INFORMATION: Primer set 15_Reverse primer
<220> FEATURE:
<221> NAME/KEY: misc_feature
<223> OTHER INFORMATION: Reverse primer

<400> SEQUENCE: 30
acgttggatg ttccacattg gtgatcagcg                                    30

<210> SEQ ID NO 31
<211> LENGTH: 30
<212> TYPE: DNA
<213> ORGANISM: Artificial Sequence
```

```
<220> FEATURE:
<223> OTHER INFORMATION: Primer set 16_Forward primer
<220> FEATURE:
<221> NAME/KEY: misc_feature
<223> OTHER INFORMATION: Forward primer

<400> SEQUENCE: 31
acgttggatg caaacggcgt cactttggtc                                     30

<210> SEQ ID NO 32
<211> LENGTH: 30
<212> TYPE: DNA
<213> ORGANISM: Artificial Sequence
<220> FEATURE:
<223> OTHER INFORMATION: Primer set 16_Reverse primer
<220> FEATURE:
<221> NAME/KEY: misc_feature
<223> OTHER INFORMATION: Reverse primer

<400> SEQUENCE: 32
acgttggatg tgaaatgtgg gcccaagacg                                     30

<210> SEQ ID NO 33
<211> LENGTH: 30
<212> TYPE: DNA
<213> ORGANISM: Artificial Sequence
<220> FEATURE:
<223> OTHER INFORMATION: Primer set 17_Forward primer
<220> FEATURE:
<221> NAME/KEY: misc_feature
<223> OTHER INFORMATION: Forward primer

<400> SEQUENCE: 33
acgttggatg cgatttcgat cgggatgttg                                     30

<210> SEQ ID NO 34
<211> LENGTH: 30
<212> TYPE: DNA
<213> ORGANISM: Artificial Sequence
<220> FEATURE:
<223> OTHER INFORMATION: Primer set 17_Reverse primer
<220> FEATURE:
<221> NAME/KEY: misc_feature
<223> OTHER INFORMATION: Reverse primer

<400> SEQUENCE: 34
acgttggatg caatcacgat cccctcaatc                                     30

<210> SEQ ID NO 35
<211> LENGTH: 30
<212> TYPE: DNA
<213> ORGANISM: Artificial Sequence
<220> FEATURE:
<223> OTHER INFORMATION: Primer set 18_Forward primer
<220> FEATURE:
<221> NAME/KEY: misc_feature
<223> OTHER INFORMATION: Forward primer

<400> SEQUENCE: 35
acgttggatg aggcaaagga aaatcgaccg                                     30

<210> SEQ ID NO 36
<211> LENGTH: 30
<212> TYPE: DNA
<213> ORGANISM: Artificial Sequence
<220> FEATURE:
<223> OTHER INFORMATION: Primer set 18_Reverse primer
<220> FEATURE:
<221> NAME/KEY: misc_feature
```

<223> OTHER INFORMATION: Reverse primer

<400> SEQUENCE: 36
acgttggatg ttgacaaact gaaacaccgc                                30

<210> SEQ ID NO 37
<211> LENGTH: 29
<212> TYPE: DNA
<213> ORGANISM: Artificial Sequence
<220> FEATURE:
<223> OTHER INFORMATION: Primer set 19_Forward primer
<220> FEATURE:
<221> NAME/KEY: misc_feature
<223> OTHER INFORMATION: Forward primer

<400> SEQUENCE: 37
acgttggatg acaaccggcc gcagcgttt                                 29

<210> SEQ ID NO 38
<211> LENGTH: 30
<212> TYPE: DNA
<213> ORGANISM: Artificial Sequence
<220> FEATURE:
<223> OTHER INFORMATION: Primer set 19_Reverse primer
<220> FEATURE:
<221> NAME/KEY: misc_feature
<223> OTHER INFORMATION: Reverse primer

<400> SEQUENCE: 38
acgttggatg aagaacaccg aaagtggctg                                30

<210> SEQ ID NO 39
<211> LENGTH: 30
<212> TYPE: DNA
<213> ORGANISM: Artificial Sequence
<220> FEATURE:
<223> OTHER INFORMATION: Primer set 20_Forward primer
<220> FEATURE:
<221> NAME/KEY: misc_feature
<223> OTHER INFORMATION: Forward primer

<400> SEQUENCE: 39
acgttggatg tgcattggcc actaaagctc                                30

<210> SEQ ID NO 40
<211> LENGTH: 30
<212> TYPE: DNA
<213> ORGANISM: Artificial Sequence
<220> FEATURE:
<223> OTHER INFORMATION: Primer set 20_Reverse primer
<220> FEATURE:
<221> NAME/KEY: misc_feature
<223> OTHER INFORMATION: Reverse primer

<400> SEQUENCE: 40
acgttggatg tcgatgacta tctgcggatg                                30

<210> SEQ ID NO 41
<211> LENGTH: 30
<212> TYPE: DNA
<213> ORGANISM: Artificial Sequence
<220> FEATURE:
<223> OTHER INFORMATION: Primer set 21_Forward primer
<220> FEATURE:
<221> NAME/KEY: misc_feature
<223> OTHER INFORMATION: Forward primer

<400> SEQUENCE: 41
acgttggatg acccatttgc cgaacgtgtc                                30

<210> SEQ ID NO 42
<211> LENGTH: 30
<212> TYPE: DNA
<213> ORGANISM: Artificial Sequence
<220> FEATURE:
<223> OTHER INFORMATION: Primer set 21_Reverse primer
<220> FEATURE:
<221> NAME/KEY: misc_feature
<223> OTHER INFORMATION: Reverse primer

<400> SEQUENCE: 42
acgttggatg tgcttggcga ctttgtgcag                                30

<210> SEQ ID NO 43
<211> LENGTH: 29
<212> TYPE: DNA
<213> ORGANISM: Artificial Sequence
<220> FEATURE:
<223> OTHER INFORMATION: Primer set 22_Forward primer
<220> FEATURE:
<221> NAME/KEY: misc_feature
<223> OTHER INFORMATION: Forward primer

<400> SEQUENCE: 43
acgttggatg agcgtgaaga agacgacga                                 29

<210> SEQ ID NO 44
<211> LENGTH: 30
<212> TYPE: DNA
<213> ORGANISM: Artificial Sequence
<220> FEATURE:
<223> OTHER INFORMATION: Primer set 22_Reverse primer
<220> FEATURE:
<221> NAME/KEY: misc_feature
<223> OTHER INFORMATION: Reverse primer

<400> SEQUENCE: 44
acgttggatg gtctgttgtc attacgggag                                30

<210> SEQ ID NO 45
<211> LENGTH: 30
<212> TYPE: DNA
<213> ORGANISM: Artificial Sequence
<220> FEATURE:
<223> OTHER INFORMATION: Primer set 23_Forward primer
<220> FEATURE:
<221> NAME/KEY: misc_feature
<223> OTHER INFORMATION: Forward primer

<400> SEQUENCE: 45
acgttggatg acatcaggtg atggtcatgc                                30

<210> SEQ ID NO 46
<211> LENGTH: 30
<212> TYPE: DNA
<213> ORGANISM: Artificial Sequence
<220> FEATURE:
<223> OTHER INFORMATION: Primer set 23_Reverse primer
<220> FEATURE:
<221> NAME/KEY: misc_feature
<223> OTHER INFORMATION: Reverse primer

<400> SEQUENCE: 46
acgttggatg cgaagggaac aatggatgtg                                30

<210> SEQ ID NO 47

```
<211> LENGTH: 30
<212> TYPE: DNA
<213> ORGANISM: Artificial Sequence
<220> FEATURE:
<223> OTHER INFORMATION: Primer set 24_Forward primer
<220> FEATURE:
<221> NAME/KEY: misc_feature
<223> OTHER INFORMATION: Forward primer

<400> SEQUENCE: 47
acgttggatg tatgccaacc gatttgcctg                                           30

<210> SEQ ID NO 48
<211> LENGTH: 30
<212> TYPE: DNA
<213> ORGANISM: Artificial Sequence
<220> FEATURE:
<223> OTHER INFORMATION: Primer set 24_Reverse primer
<220> FEATURE:
<221> NAME/KEY: misc_feature
<223> OTHER INFORMATION: Reverse primer

<400> SEQUENCE: 48
acgttggatg acatattgtc caccgcgtag                                           30

<210> SEQ ID NO 49
<211> LENGTH: 29
<212> TYPE: DNA
<213> ORGANISM: Artificial Sequence
<220> FEATURE:
<223> OTHER INFORMATION: Primer set 25_Forward primer
<220> FEATURE:
<221> NAME/KEY: misc_feature
<223> OTHER INFORMATION: Forward primer

<400> SEQUENCE: 49
acgttggatg tcttggcagc ggcatggac                                            29

<210> SEQ ID NO 50
<211> LENGTH: 30
<212> TYPE: DNA
<213> ORGANISM: Artificial Sequence
<220> FEATURE:
<223> OTHER INFORMATION: Primer set 25_Reverse primer
<220> FEATURE:
<221> NAME/KEY: misc_feature
<223> OTHER INFORMATION: Reverse primer

<400> SEQUENCE: 50
acgttggatg ccgaatttcc agtctcacag                                           30

<210> SEQ ID NO 51
<211> LENGTH: 25
<212> TYPE: DNA
<213> ORGANISM: Artificial Sequence
<220> FEATURE:
<223> OTHER INFORMATION: extension primer 1
<220> FEATURE:
<221> NAME/KEY: misc_feature
<223> OTHER INFORMATION: extension primer

<400> SEQUENCE: 51
gacctgtcct acgaaccggt gatgg                                                25

<210> SEQ ID NO 52
<211> LENGTH: 20
<212> TYPE: DNA
<213> ORGANISM: Artificial Sequence
<220> FEATURE:
```

```
<223> OTHER INFORMATION: extension primer 2
<220> FEATURE:
<221> NAME/KEY: misc_feature
<223> OTHER INFORMATION: extension primer

<400> SEQUENCE: 52
cgttgcccac gttgttggcg                                              20

<210> SEQ ID NO 53
<211> LENGTH: 23
<212> TYPE: DNA
<213> ORGANISM: Artificial Sequence
<220> FEATURE:
<223> OTHER INFORMATION: extension primer 3
<220> FEATURE:
<221> NAME/KEY: misc_feature
<223> OTHER INFORMATION: extension primer

<400> SEQUENCE: 53
caccggccaa cgtctcgggc atg                                          23

<210> SEQ ID NO 54
<211> LENGTH: 21
<212> TYPE: DNA
<213> ORGANISM: Artificial Sequence
<220> FEATURE:
<223> OTHER INFORMATION: extension primer 4
<220> FEATURE:
<221> NAME/KEY: misc_feature
<223> OTHER INFORMATION: extension primer

<400> SEQUENCE: 54
cccccgaccg gccgttcttc g                                            21

<210> SEQ ID NO 55
<211> LENGTH: 17
<212> TYPE: DNA
<213> ORGANISM: Artificial Sequence
<220> FEATURE:
<223> OTHER INFORMATION: extension primer 5
<220> FEATURE:
<221> NAME/KEY: misc_feature
<223> OTHER INFORMATION: extension primer

<400> SEQUENCE: 55
ttcaacggcg gcatcat                                                 17

<210> SEQ ID NO 56
<211> LENGTH: 17
<212> TYPE: DNA
<213> ORGANISM: Artificial Sequence
<220> FEATURE:
<223> OTHER INFORMATION: extension primer 6
<220> FEATURE:
<221> NAME/KEY: misc_feature
<223> OTHER INFORMATION: extension primer

<400> SEQUENCE: 56
gccgaaacaa gatttgc                                                 17

<210> SEQ ID NO 57
<211> LENGTH: 17
<212> TYPE: DNA
<213> ORGANISM: Artificial Sequence
<220> FEATURE:
<223> OTHER INFORMATION: extension primer 7
<220> FEATURE:
<221> NAME/KEY: misc_feature
<223> OTHER INFORMATION: extension primer
```

<400> SEQUENCE: 57
ccttctgcgt ctccaat                                                      17

<210> SEQ ID NO 58
<211> LENGTH: 17
<212> TYPE: DNA
<213> ORGANISM: Artificial Sequence
<220> FEATURE:
<223> OTHER INFORMATION: extension primer 8
<220> FEATURE:
<221> NAME/KEY: misc_feature
<223> OTHER INFORMATION: extension primer

<400> SEQUENCE: 58
gatatggggc cgcggat                                                      17

<210> SEQ ID NO 59
<211> LENGTH: 23
<212> TYPE: DNA
<213> ORGANISM: Artificial Sequence
<220> FEATURE:
<223> OTHER INFORMATION: extension primer 9
<220> FEATURE:
<221> NAME/KEY: misc_feature
<223> OTHER INFORMATION: extension primer

<400> SEQUENCE: 59
accgtaaacg ggcctaaccc tcc                                               23

<210> SEQ ID NO 60
<211> LENGTH: 18
<212> TYPE: DNA
<213> ORGANISM: Artificial Sequence
<220> FEATURE:
<223> OTHER INFORMATION: extension primer 10
<220> FEATURE:
<221> NAME/KEY: misc_feature
<223> OTHER INFORMATION: extension primer

<400> SEQUENCE: 60
ttggggctgg gaactggg                                                     18

<210> SEQ ID NO 61
<211> LENGTH: 19
<212> TYPE: DNA
<213> ORGANISM: Artificial Sequence
<220> FEATURE:
<223> OTHER INFORMATION: extension primer 11
<220> FEATURE:
<221> NAME/KEY: misc_feature
<223> OTHER INFORMATION: extension primer

<400> SEQUENCE: 61
attcacgtga aaaccctcg                                                    19

<210> SEQ ID NO 62
<211> LENGTH: 21
<212> TYPE: DNA
<213> ORGANISM: Artificial Sequence
<220> FEATURE:
<223> OTHER INFORMATION: extension primer 12
<220> FEATURE:
<221> NAME/KEY: misc_feature
<223> OTHER INFORMATION: extension primer

<400> SEQUENCE: 62
agctcagcgc gcggctggtg t                                                 21

```
<210> SEQ ID NO 63
<211> LENGTH: 23
<212> TYPE: DNA
<213> ORGANISM: Artificial Sequence
<220> FEATURE:
<223> OTHER INFORMATION: extension primer 13
<220> FEATURE:
<221> NAME/KEY: misc_feature
<223> OTHER INFORMATION: extension primer

<400> SEQUENCE: 63
caaaatacgg cgatcatcat ggg                                              23

<210> SEQ ID NO 64
<211> LENGTH: 17
<212> TYPE: DNA
<213> ORGANISM: Artificial Sequence
<220> FEATURE:
<223> OTHER INFORMATION: extension primer 14
<220> FEATURE:
<221> NAME/KEY: misc_feature
<223> OTHER INFORMATION: extension primer

<400> SEQUENCE: 64
ccaccagtac ttgccgc                                                     17

<210> SEQ ID NO 65
<211> LENGTH: 17
<212> TYPE: DNA
<213> ORGANISM: Artificial Sequence
<220> FEATURE:
<223> OTHER INFORMATION: extension primer 15
<220> FEATURE:
<221> NAME/KEY: misc_feature
<223> OTHER INFORMATION: extension primer

<400> SEQUENCE: 65
atcggggtga cgatgag                                                     17

<210> SEQ ID NO 66
<211> LENGTH: 22
<212> TYPE: DNA
<213> ORGANISM: Artificial Sequence
<220> FEATURE:
<223> OTHER INFORMATION: extension primer 16
<220> FEATURE:
<221> NAME/KEY: misc_feature
<223> OTHER INFORMATION: extension primer

<400> SEQUENCE: 66
gccgaggagc ccgcgtaacc gt                                               22

<210> SEQ ID NO 67
<211> LENGTH: 18
<212> TYPE: DNA
<213> ORGANISM: Artificial Sequence
<220> FEATURE:
<223> OTHER INFORMATION: extension primer 17
<220> FEATURE:
<221> NAME/KEY: misc_feature
<223> OTHER INFORMATION: extension primer

<400> SEQUENCE: 67
tgttgatcgg cccgaggc                                                    18

<210> SEQ ID NO 68
<211> LENGTH: 20
```

```
<212> TYPE: DNA
<213> ORGANISM: Artificial Sequence
<220> FEATURE:
<223> OTHER INFORMATION: extension primer 18
<220> FEATURE:
<221> NAME/KEY: misc_feature
<223> OTHER INFORMATION: extension primer

<400> SEQUENCE: 68
gcgggcgtgg aacgctggtc                                               20

<210> SEQ ID NO 69
<211> LENGTH: 20
<212> TYPE: DNA
<213> ORGANISM: Artificial Sequence
<220> FEATURE:
<223> OTHER INFORMATION: extension primer 19
<220> FEATURE:
<221> NAME/KEY: misc_feature
<223> OTHER INFORMATION: extension primer

<400> SEQUENCE: 69
agcgtttcca ggtcaccgca                                               20

<210> SEQ ID NO 70
<211> LENGTH: 17
<212> TYPE: DNA
<213> ORGANISM: Artificial Sequence
<220> FEATURE:
<223> OTHER INFORMATION: extension primer 20
<220> FEATURE:
<221> NAME/KEY: misc_feature
<223> OTHER INFORMATION: extension primer

<400> SEQUENCE: 70
ccagagcgca acaacaa                                                  17

<210> SEQ ID NO 71
<211> LENGTH: 18
<212> TYPE: DNA
<213> ORGANISM: Artificial Sequence
<220> FEATURE:
<223> OTHER INFORMATION: extension primer 21
<220> FEATURE:
<221> NAME/KEY: misc_feature
<223> OTHER INFORMATION: extension primer

<400> SEQUENCE: 71
cacgctggca tcaagttc                                                 18

<210> SEQ ID NO 72
<211> LENGTH: 22
<212> TYPE: DNA
<213> ORGANISM: Artificial Sequence
<220> FEATURE:
<223> OTHER INFORMATION: extension primer 22
<220> FEATURE:
<221> NAME/KEY: misc_feature
<223> OTHER INFORMATION: extension primer

<400> SEQUENCE: 72
gaagacgacg aggacgactg gg                                            22

<210> SEQ ID NO 73
<211> LENGTH: 18
<212> TYPE: DNA
<213> ORGANISM: Artificial Sequence
<220> FEATURE:
<223> OTHER INFORMATION: extension primer 23
```

```
<220> FEATURE:
<221> NAME/KEY: misc_feature
<223> OTHER INFORMATION: extension primer

<400> SEQUENCE: 73
gacgattccg ggcatgcg                                                    18

<210> SEQ ID NO 74
<211> LENGTH: 17
<212> TYPE: DNA
<213> ORGANISM: Artificial Sequence
<220> FEATURE:
<223> OTHER INFORMATION: extension primer 24
<220> FEATURE:
<221> NAME/KEY: misc_feature
<223> OTHER INFORMATION: extension primer

<400> SEQUENCE: 74
tgcctgcctg gtatgac                                                     17

<210> SEQ ID NO 75
<211> LENGTH: 17
<212> TYPE: DNA
<213> ORGANISM: Artificial Sequence
<220> FEATURE:
<223> OTHER INFORMATION: extension primer 25
<220> FEATURE:
<221> NAME/KEY: misc_feature
<223> OTHER INFORMATION: extension primer

<400> SEQUENCE: 75
ggcatggacg ggatcgg                                                     17

<210> SEQ ID NO 76
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 76
tgccgggccg cctccagtcg acgtcgggta gtcgctaccg ccggcaccac cacccggcgc      60
accagctggt cctgctcggc gaatagctcg gcggccgccg cctcggctcg caatcgttgt     120
accccaccgg tgatcgcgtt gaccgtcatc acgcccgcta ccagtagcgc gtcgatattg     180
ctgccgacaa tcgccgatgc tgcggcgccc accgccagga tcggagtcag cggatcggcc     240
agttcatggc gggtggccac cgccagctgc gccaaggttc gtgccgggcc gcgcagcggc     300
tccatcaccg gttcgtagga caggtcgtcc agaatgcgcc gccaggccgg gattccgggt     360
tcgacggcca agggtcggga gccgccggct agccgcgagt agacgatctc ggggtccagc     420
gcgtgccagg cggtcagcgg ttgcggggtg gggtcgggca tccgcagcac cttggcggcc     480
gaccacattc cggacaccaa agccgttgcg gcagcggcat tgaccggatt gagccagcga     540
cggaagctgg ctgggttggt ggttttgtcc tgctcaccgg tgaccaacaa cagcccggcc     600
a                                                                    601

<210> SEQ ID NO 77
<211> LENGTH: 601
<212> TYPE: DNA
<213> ORGANISM: Mycobacterium tuberculosis
<220> FEATURE:
<221> NAME/KEY: variation
```

```
<222> LOCATION: (301)..(301)
<223> OTHER INFORMATION: SNP

<400> SEQUENCE: 77
agcgttggga cccagcgaga tgaggtgctg catttccagg gacgcgatga cggcgctctg      60
cgaatagccg aacacggtga cgtggtttcc ggcgttgatt tgctcccaaa tcgcgccgtc     120
gagaatctgt aggcccaact gcaccgaggt ttggaagggc agggatttga cgccggtgat     180
cggatatagc tcttcgggcg tcaccagcgc tttgacgacc ggattcgaga cgacggggtc     240
gatgaacaag gtcgtgatgg cgttgacata actcggcgtg ggtatcggtg acccggtgcc     300
acccatgatg atcgccgtat tttggttgaa cattggcggt agcaccgggg gtgaggttgg     360
cttaaagagt ccggccgtcg cctcctgcac cagcgcgctc gtgttggtgg cctcggcatt     420
gacaaatgcg tttgcggccg ccgccaacct ctgggtgaat tcgttgtgaa acgccgcaac     480
ctgtgcgctg atcgcctgga actgctggcc gtacgcgccg aacagcgtgg caagggccgt     540
ggacacttcg tccgcggcag ccgccgccag gccggttgtc ggggccgcga cggccgccgt     600
a                                                                     601

<210> SEQ ID NO 78
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 78
ccgacaacac cggcccaccc ggcagcgtgg tgctcagcga gttggcggcg tagaaggcgg      60
cctccgaccg ccattgcttg acgtgcaccc cggcggattt cagcagggtt cgctgaatct     120
gggcgaagct gtgcatcgag gcgcccgcgg ctgccaccgc ggccagcaac caccaccact     180
tggcgcgata caagctcacc caggccttgg cgagctggtc ccagcccaac gccacctcta     240
tagcaagcac gattgcgacg atggccagta ccgcccatcg caaccaccag tacttgccgc     300
acggggtac gccctcagcg gggggtgccc ccacccgcgt gcgagggagt gccccacgc      360
gctggcggag gttgcgggcg ggggcgtcgt gcgacacgtg cttaagggta accgtgcagg     420
tggcgccgta atcgcgatac atcgctaacc gtgtcagcct cgttgggggg tcgtgaccgg     480
atcgtgccgc ctggcaaagt aactatgcgg gctcgacgcg acccgccgcg accttacgac     540
gccgccgttc ccgttacgct tgccggatgt cggcgagcct ggatgacgct tcggtcgcac     600
c                                                                     601

<210> SEQ ID NO 79
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 79
cgaggccagg ttccaaaagc ccgaagcgcc gccgccgaag ttgccgaagc ccgaggcggt      60
gccggcgcca cgttgaagaa agcccgacga cgggctggtg gtcgagttcc cgaagcccgg     120
ggccgccgga atcttgatga gcgggatgct gacgcccccc accatgccgg tgaggttgcc     180
```

```
gtcgatcgtg gtggttggtc cgcccacggt gatcgtcacc gtgggaaggg tgagcgtgga      240
ttgcgggagc tcgaccgggc cgtagtaaac aacgaaggga acaatggatg tgaagggcaa      300
gcgcatgccc ggaatcgtca tcacgcttcc gggcatgacc atcacctgat gtatcggcat      360
gctgaatagc tgcgcgttta tcggaatggc gggaatctcg agggcgatat cggcaccgat      420
caggccttgg tagtcgcccc gccacaagac gccgttgctg tagttgccgg cgatgaaggc      480
gccggtgttg acgttgccgg tgttggccac tccagtgttg tagtcgccgg tgttgaagta      540
gccggtgttg tagttacctg cgttgaagct gccggtgttg tagttgccgg tgttgaagtt      600
c                                                                      601
```

<210> SEQ ID NO 80
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 80

```
ttgaacaacc cgacgtttcc gctgccggag ttgaacaggc cgatgttgtg gctgcccgag       60
ttgaagctgc cgaacccgat ctgtccgttg ccggtgagcc cgatgccgac attgttgctg      120
cccgtattcc caaagccgac attgttgctg ccggtgttcg caaagccgat gttgtggccg      180
cccaggttgg ccaaacccag gttgtcgctg cccaggtttg caaagccgag gttgtagctg      240
cccaaattgc cgaagccgac gttgaacacg ccgacgtttc cgttgcccac gttgttggcg      300
gcgacgtttg ccaagccgag attgaagccc gccgcgctcg gggggccggc agcggctgcc      360
gcggcgctgt tcagccgctc cgataggccc gccagcttct tcagctgctg ggtgaacggc      420
atcaacgcgg agacggccgc cgacgctcca gcgtgatagc caaccatcgc ggccacatcc      480
tgggcccaca tccgctcata gcggcctcg gtggccgcga tcgccggagc gttgaatccc       540
agcagattcg agctcaccag cgacaccagc acggcgcggt tggccgcgac gatcgccgga      600
t                                                                      601
```

<210> SEQ ID NO 81
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 81

```
agtcgccggc gttgccgaat ccgaagttgt agctgcccag gttgcctagg ccgatgttgt       60
agttacccag gttcgccggg ccgatgttgt atgagccctg gtttccgccg aagacgttga      120
agctgccgag gttgccgctg ccgaggttga agctgccgat gttcgccaag ccggcgttgc      180
tgtcgcctac gttggagaag ccgacgttga attggccgat gttttccagg ccgaggttga      240
acatcgacat cccggtcgcc tggtcgtgga agaaccccgc gaggttgctg ccgatgttga      300
gcatgcccga gacgttggcc ggtgccccga tgccggtgtt gaatacgccc gagacggtat      360
cgcccaggtt cgccagtccc gattgcagcg agccgtagtt gttgaagccc gaggtcgcgg      420
agttcgcgac gttctggaag ccggaaatgt tggcgccgat gttggcgatg cccgatacgg      480
ttccggggcc gccgttgaag aagcccgagg acggatcggt ggtggcgttg aaaaagcccg      540
```

```
tggtagccgc aatgttgacg aacgtgacat cgaagggacc gacgcttgcg gtggccggga    600
t                                                                   601

<210> SEQ ID NO 82
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 82
taaagctcaa cggctacaac accgcccagt tcggcaagtg ccacgaagtc ccggtctggc     60
agaccagccc ggtcgggccg ttcgacgcgt ggcccagcgg cggcggtggt ttcgaatact    120
tctacgggtt tatcggtggc gaggctaacc agtggtatcc gagtctgtac gagggcacca    180
cgccggtcga ggtgaaccgc acgcccgagg agggttacca tttcatggcg gacatgaccg    240
acaaggccct cggctggatc ggacagcaga aggcactggc ccccgaccgg ccgttcttcg    300
cgtacttcgc cccgggcgcc acccacgcgc cccaccacgt tccgcgggag tgggccgaca    360
agtaccgggg ccgcttcgat gtgggctggg acgcactgcg agaggaaacc ttcgcccggc    420
aaaaggaact cggggtgatc ccggcggact gccagctgac cgcgcggcac gccgaaatcc    480
cggcgtggga cgacatgccg gaggacctca aacccgtgct atgccggcag atggaggtct    540
acgcgggctt tctggaatac accgaccacc acgtcggccg gctcgtcgac ggcctgcagc    600
g                                                                   601

<210> SEQ ID NO 83
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 83
gttggcgaag cccgagattt gtaaattacc aacgttttgg gcgccggagt ttcccctacc     60
agaattattg aaacccgaat ttccactgcc ggcgtttccg aatcccgagt tttcgcccag    120
cccatcggta gtattgccga aaccggtgtt caggttgccc gcgttaaagc cgcccgtgtt    180
gatattgcca gaatttgcga agccggtgtt cgtcaggcca gagttcaaga aaccagaatt    240
agcgtctcct ccgttgaagc tgcctgagtt gaatgcaccc gagttgaagc taccggtgtt    300
gatgatgccg ccgttgaagt tgccggtgtt gaaatcgccc gcgttcccta tgccggtatt    360
ggcctgacct gagttgccaa agccagtgtt gacgcttaac gcgttcccga agccggtgtt    420
gataaagccg gagtttccga agccggtgtt gatgttgcct gagttggcta cgcccgtgtt    480
ggtgacgccc gagttgccca cgccgaagtt gccgctgccc gagttgaaga agccgatgtt    540
cccggtgccc gagttaccaa atcctatatt accgctaccg gaattcagtc cgccaaagcc    600
g                                                                   601

<210> SEQ ID NO 84
<211> LENGTH: 601
<212> TYPE: DNA
<213> ORGANISM: Mycobacterium tuberculosis
<220> FEATURE:
```

```
<221> NAME/KEY: variation
<222> LOCATION: (301)..(301)
<223> OTHER INFORMATION: SNP

<400> SEQUENCE: 84
ttgtccgcag gagtgttgag tgaggcggcc agcgccgtgt agtagtcacg gtgacgtgcg      60
tgcacatcgg cctcgccgga gtcgcccagt ttttccagcg cgtaccgacg caccgtttcc     120
agcagccggt accgcgtgcg gccctggcag tcgtcggcca ccaccagcga cttgtctacc     180
agcagggtca gctgatcaag caccgaaaac ggatccaggt cgctaccggc ggcgaccgcc     240
cgcaccgcgg cgaggtcgaa cccgccgaca aatggcgcca gtcgccgaaa caagatttgc     300
ccggtctcgg tcagcagtgc atgcgaccaa tcgatcgagg cgcgaagtgt ctgctggcgc     360
tgcaccgcgc cccgcacacc gccggccaac agcggaaaac agtcgtccag accgtcggca     420
atctcgagcg gtgacatcga ccgcacccgt gcggcagcga actcgatcgc cagcggtatg     480
ccgtctagcc gccggcagat ctcgccgacg gccgcggcgt tgtgattggc gatggtgaac     540
ccgggctgaa ctcggctggc tcggtcagca aacaattcga ctgcttcgtc ggttatcgac     600
a                                                                     601

<210> SEQ ID NO 85
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 85
tccaactcga agattgttgt cccgattggc cattgcaatc ggaatgcacg ggaatccaat      60
cctgcagcca agatgaccac ctgcttcatg ccggcggccg ttgcccggga gaaatactcg     120
tcgaaatacc tggtgcgggc accttggaag ttgacgaaat gctcaccgaa gtccccggtt     180
gtcagatagt gatcgggcag cttgccgtcc aatacgtcgg cccattcacc acctgcggca     240
cggcagaaaa cctcggcata gggatcgatg gccagcggat cggccttctg cgtctccaat     300
actcttgcgg cggctaccaa tagtcctgtc gaaccaacac tcgtggtgac atcccagcta     360
tcgtcctcgg tccgcattca tcgaactcta gttgctccag tccgcccacc gctgtcggta     420
tcccagcgca gtcggccgtg cacacatatc tgcgcggtgg acttggtact tctacgcgca     480
ttcgccgatg ttttgcgatc cgcggcgggt ctatggtgcc atttatgtgc caggatcggt     540
cttcaataac aacgtcgcga agcgaggggt cgtgacgtga gagggctcgc ttatgccggc     600
g                                                                     601

<210> SEQ ID NO 86
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 86
gagcgctacc ttggatgttg agggagttga actccggcgg aaaaattgtg aaatccattg      60
tcgctcaacc gctgtctagg tggaggtgcc cgcgcggttg gctaattcgg tgagccaata     120
cgaagtcttg ctggtctgaa gtgtttggac aaatgactcg tggatcacat gggcctggcg     180
```

```
cgcgatcgcc ttgtacagct cgccgtgcat ggaaaacagc atcgacgtca cgatggacac      240
aagatcgtgg gcgggggatt ccacattggt gatcagcggc gtgaccccgt catcatgggc      300
actcatcgtc accccgatct cgtggaggtt ggcggccgtt tccccaatcg aatcgggccg      360
tgtggtgaca aaagacacgc gtgcatctcc ttccactgac gtggtctgat ggtgggggtc      420
agcgacgact tggggttccg cacggcattg tagacggaat cgttcactaa ggtattttca      480
ccataacggg ttcggtcaca aaacggtagc gattctgttg aggaattttt tcgacgctcg      540
cccggtaggg tgcctccatg tctgagacgc gcggctgct gtttgttcat gcacaccccg       600
a                                                                      601
```

<210> SEQ ID NO 87
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP
<400> SEQUENCE: 87

```
tctgtgggtg gtcccggatg tcgcggcccg cggagccgat cttgcccatg tcccagtggt       60
gacgctggtc ggaagcgccc ggcactattg gggcgcggtg gcggcggtgt tggcggcagt      120
gtgtgctttg ctcgctgccg tcttcttgat gagttcggcg gcgattcgcg ggtcggctgg      180
cgaggacatg gcgagatatg cggcgccccg cgcccgccgg tcgattgccc ggcgccagca      240
ctcgaatgcg gccggccggg cggctccgca agacgacggg ccggatatgg ggccgcggat      300
atcggagcga atgatttggg aagctcttga cgagggccgt gacccgaccg atcgggagca      360
ggagtctgac accgagggggc ggtgacggac cgcgcgctga cggtcgctac ccttcatgga     420
cgtcgtcgaa attgacgagc gcgtgtgggt gacagtggga agggaacggc aggcatgagt      480
ccggcaaccg tgctcgactc catcctcgag ggagtccggg ccgacgttgc cgcgcgtgaa      540
gcctcggtga gcctgtcgga gatcaaggct gccgccgctg cggcgccgcc gccgctcgac      600
g                                                                      601
```

<210> SEQ ID NO 88
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP
<400> SEQUENCE: 88

```
aacccacggt gttgtaaaac agctgtgata tcggcagata ccagttgatg aaccattcca       60
gccaccccgg ggtcgcggcg gcggtcaacg cggacgacag gggcgaggtg aggcccagca      120
gcgtgttggg caagtgggcg atcagctccg ctattgcgct ctgcgccgcg ccggctgagg      180
tgccggcggc tttggcgact gcggacaact gcgtcgccgc ggcggatggg ctggtggtgt      240
tcggcggcgg ggcaaacggc gtcactttgg tcgcggtcgc cgaggagccc gcgtaaccgt      300
gcatggccat ggcgtcttgg gcccacattt cagcgtattg agcttcggtg gccgcgattg      360
atgcggtgtt ttgaccgaac acgttatgcg tgaccagcga cgtgagccgc gcgcgattgg      420
ccgcgatcag cggcgggggc acaatggcgg caaacgcggt ttcgtaagcg gccgccgccg      480
```

```
cacgcgcctg actggctgcc tgctcagctt ggatggcggt ggctcgcatc cacgccacat    540
acggggcgac cgcttcgacc atcaacgtcg acgccggacc cagccattct tcggtttgca    600
g                                                                   601

<210> SEQ ID NO 89
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 89
ccggccacct gtggcaccag cgtctatgtc tacccattcg accttgccga cgaggtcttt     60
acctgggccc gcgcggtcag cgccgaagtc gaccctcggg tcgagctgca agcccttgcc    120
tcccgcggtg aaccgagcat gggcatcgac gtccccgtca tctcccttgc ctcgcccgct    180
ttcgctgact cgcccgaaga ggccgaacag gccctcgccc tgttcggcac ctgcccggtt    240
gtcgagcagg cactggtcaa agtcccttat atgccaaccg atttgcctgc ctggtatgac    300
atcgcgatga cccactacct gtcagaccat cactacgcgg tggacaatat gtggacgtcg    360
gcgtccgctg aggacctgct gccgggtatc cgctcaatcc tggacacgct gccccgcat    420 ccggcgcact tcctctggct gaactggggt ccatgccctc ccgtcaaga catgcctat     480 agcatcgaag ccgacatcta cttggcgctc tacggctcct ggaaggatcc ggccgacgag    540
gcgaagtacg ccgactgggc gcggtccac atggccgcga tgtcgcatct ggcggtcggc    600
a                                                                   601

<210> SEQ ID NO 90
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 90
tgttaccgac gccggagtga aaggccgatg tcgctaggcc cagcgtgctg gtgttgtaga     60
ggcctgagac tgtgttgccg aagttcaaga ttcccgatgt cagtggcccg acgttaagga    120
atccggagtt gccgagattc ccagcaatgt tccagaagcc agatccgccc gaaccgacgt    180
tcccgaaacc cgatgtgccg cccgtaccgc tgttgaagaa gcccgatgac ggggtggtgg    240
tcgagtttcc gaagcctggg gtgcccgcga tttcgatcgg gatgttgatc ggcccgaggc    300
ggccggacac gtcgatgccc aacgggattg agggatcgt gattggcggg gtagtgaggg    360
ggccgatggc gccgcccaca tcaatacccca acgggattgc cggaagtgag tagccatccg    420
ggaacaccgt aaacgggcct aaccctccgc ccacatcaat acccaacggg attgccggaa    480
gtgagtagcc atccgggaac accgtaaacg ggcctaaccc tccgcccaca tcaataccca    540
acgggattgc cggaagtgag tagccatccg ggaacaccgt aaacgggcct aaccctccac    600
c                                                                   601

<210> SEQ ID NO 91
<211> LENGTH: 601
<212> TYPE: DNA
<213> ORGANISM: Mycobacterium tuberculosis
```

```
<220> FEATURE:
<221> NAME/KEY: variation
<222> LOCATION: (301)..(301)
<223> OTHER INFORMATION: SNP

<400> SEQUENCE: 91
gctgccggac acgtcgatgc ccaacgggat tgaggggatc gtgattggcg gggtagtgag      60
ggggccgatg gcgccgccca catcaatacc caacgggatt gccggaagtg agtagccatc     120
cgggaacacc gtaaacgggc ctaaccctcc gcccacatca atacccaacg ggattgccgg     180
aagtgagtag ccatccggga acaccgtaaa cgggcctaac cctccgccca catcaatacc     240
caacgggatt gccggaagtg agtagccatc cgggaacacc gtaaacgggc ctaaccctcc     300
gcccacatca atacccaacg gaatagccgg caaactataa ccacccgata agaaggtgat     360
gggaccgatt tgaccactca ctgtcacgta atctggaggg aatccgggga aaaatggcgg     420
aatcgcggga atctcaggag tgcctagctg tatcgatatg ctacccgggc ctatgctgcc     480
aacggtggga tttacgccga ataagccgat cgcaagcgga gacgcgggga tcgaaatcga     540
tcccacgtta atgacctgga acgccgatag ctctaggcca atagaattta gagtgatcgg     600
c                                                                   601

<210> SEQ ID NO 92
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 92
ccatgcggtg ccgcggtggt ccagccagcg ccctgcagtg tgctggtgct cgataccagg      60
ttggcctgtc ccgcccagct gggcggcacc gacaatgcgc cgattgacga cgcccgacta     120
aggccggcgg ctagcggagc cgcacccaga ccggccgcga tcggcgcctc gccgacggcc     180
gcctccgccg cccccagctc cgataggccc gcgccctcca agccctcctc gagggcgggct     240 tcctcggcag ccggaagaag accaccgctg gccagcccta gcaagtccga cgcggcggag     300
acccagttcc cagccccaat gttgaagata ttggcaatat ctgaaatcca ggagggcacc     360
ttcccgggcg tggaacccaa gatgctcgcg atacccgaca acggcgaagc ggccgcggat     420
gagttggcgg cctcggtggc cgcataggtg ccagcgctga ccccagggt cttcacaaac     480 aggtcgtata ccgcagctgc ttcagcactg acctgctggt agagagtgcc gtacgcggtg     540
aacaacggcg cctgtagcac tgatatctca tcagcggcgg cgggaatcac gcccgtggtg     600
g                                                                   601

<210> SEQ ID NO 93
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 93
acgtcgagcc aaccccactt cagtgggtag gtgaactcgt ccagcagata gaagtcgtga      60
cgttgcgtgg ccagccggag cgcgatctcg gcccaaccgt ccgccgccgc ggccgcacga     120
```

| | |
|---|---|
| tcgacgtcgg tgccggcctt gcgagacgta cgtgtccagg accagcccgc acccatcttg | 180 |
| tgccactcca ccgctccgcc gatcccgtgc tggtcgtgca gccggcccag ttgacgaaac | 240 |
| gccgcctcct cacccacttt ccacttagcg ctcttgacaa actgaaacac cgcgatgtcc | 300 |
| cgaccagcgt tccacgcccg caacgccatt ccgaacgccg cggtcgattt tcctttgcct | 360 |
| tcaccggtgt gtaccgccag tatcggcatg ttgcgccggg cccgggtggt caggccatcg | 420 |
| ttgggcactg cgagcggatt gccctgcggc atgtgtggtt acctatccat cgtcaagcca | 480 |
| cgccacgcac ggcatgcact agataatccg cgtgcaactg ctccaaccga accaccggcg | 540 |
| cacccagctg acgagccagt tgcgctgcca aacccagccg tacatacgac gtttcgcagt | 600 |
| c | 601 |

<210> SEQ ID NO 94
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 94

| | |
|---|---|
| ctgcgagtgg gccgaccgat aggcccgatg ctggcacaga ccgcgaccag cgtccatgat | 60 |
| gcactcgaac gtcacggcgg cacaaccatt ttcgaggcta aactagacgg cgcgcgagtg | 120 |
| cagatccacc gggcaaacga ccaggtcagg atctacaccc gaagcctgga cgacgtcact | 180 |
| gcccggctgc ccgaggtggt ggaggcaaca ctggcactgc cggtccggga tctagtggcc | 240 |
| gacggcgagg cgatcgcgct gtgcccggac aaccggccgc agcgtttcca ggtcaccgca | 300 |
| ccacggttcg gccgatcggt cgatgttgcg gctgcccgcg cgacgcagcc actttcggtg | 360 |
| ttcttcttcg acatcctgca tcgggatggt accgacttgc tcgaagcgcc gaccaccgag | 420 |
| cggctggccg ccctggacgc actggtgccg gctcggcacc gcgtggaccg gctgatcacg | 480 |
| tccgatccaa cggacgcggc caacttcctg gatgcgacgc tggccgccgg ccacgagggg | 540 |
| gtgatggcca aggcaccggc cgctcgttac cttgcgggtc gccgcggagc gggctggctg | 600 |
| a | 601 |

<210> SEQ ID NO 95
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 95

| | |
|---|---|
| acggtgaggc cggccgggaa caaggccaag gacgatgtgg acagattgaa agtcgcgccg | 60 |
| aacgggccgg ggatcgtgcc cgggccgccg tagctgccga tgatgggtcc attgatctgc | 120 |
| aggtcgctga tgctgaggta gaacgacccg gaggggaatt tcgcgccggg tgggcctagc | 180 |
| ggcgggccgt agtggtcgat cgtgatgaac gggtccggca agacgaccgg gtccgcggtg | 240 |
| atttctgcca tggcggtttg cccgaaaaga acaaacgcgg gattcacgtg aaaaccctcg | 300 |
| tggccgacgg ttccggtcac gtggatcggg atcgcgggaa tggtgatctc cgggagagtg | 360 |
| aattcgcgga tcccgatgaa tccccggtg atttgtatgt cgaatgccgg aatatcgatg | 420 |
| ggctggacgt ggatgggacc gatcccgcca atcacctgca ggtcaatggg gatttcggaa | 480 |

```
atggtgaaaa gggtgccggg ggtgaagggg gccaggacgt tgatgttgtt gcccgttaag    540
aagaaaccgg tgttgtggct tcccgaattg aatacgccca aattcccggt gccggagttg    600
a                                                                    601
```

<210> SEQ ID NO 96
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 96

```
acaagcgcgg tagcccgctc gacatcgctt gctgtcattg cggcaggtgc ttgatagagg     60
gccgccaatt cggtcgccgc ttcggatcgc gagttcaggg cggcaacaac tggcagtgtc    120
gccttacgtc gggcaaggtc gttgccgacc ggctttcccg tcacaccagg gtcaccccag    180
atgccgatca gatcgtcgac gcattgaaac gcaagaccca actcatggcc aaaacgctcc    240
aacgcagcaa tcgtcgcgtc gtctgcattg gccactaaag ctcccagagc gcaacaacaa    300
tcggtcaggg cggccgtctt gcccgcggcc atccgcagat agtcatcgac tgtaacttcg    360
ggctgtccct ccaataaaca atcctcaaac tggccgatac acaagtccag gcacgacatc    420
tgcaatcgcc ttatcgccct gaccgccaca cactcgtcgg tcaggccggt cagtatccga    480
acggccgtgg cgtgcaacgc atctcccaac aggatcgcga cgcccacacc ccacacactc    540
cataccgtcg gccgtcccct gcgagtcgca tccccatcca tcacatcgtc atgcaacaac    600
g                                                                    601
```

<210> SEQ ID NO 97
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 97

```
gtcagccagt cgttgcgaac atcgtcgtcc acgtagggct gtatctgttg gcgaaccact     60
tcgacggccg tcggccgatc tgccccctcc gtcgtgagcg cttcggccgc agccaaccat    120
gccggccgct gcgccagggc acgctcgtcg atcgcaatgg ccgtcgcgac tttggagtcc    180
accagctgcc agaggttgtc gcgcagcgat tcgcagcgtt gggccgcggc acggacttcg    240
gtgaccaccg aatttccagt ctcacagtga cgctgcacaa agtgcaccgc cgcgtcggcc    300
tccgatcccg tccatgccgc tgccaagacg gcgacctggc tacgctccat ccgcagcgcc    360
tccatgagca cactggcggc agcccgcagc tgcgcgcagt cagcgtcgag cgcgtgcagg    420
tcaagtccgt cttcgctgcc gtaccagtcg tggatctggg cagggtaggc ggtcaggtcg    480
ggatgttggt agcccaccag gtggcaagcc cgcacgtagc tttgcgtgtg ctcggctgcg    540
ggcctgccct cggcgagacg ctcagcgacg ttcaaccggt cagccaccct cacccgatcc    600
g                                                                    601
```

<210> SEQ ID NO 98
<211> LENGTH: 601
<212> TYPE: DNA

-continued

<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 98
cgccagcacc gcggggctcg ccgccggggt cgtggcggtc caaacggccg gaaccttcaa 60
tcccccgacc gacgccgcct gaccgacggc gcccgcaacg ccgctcaggc cagcactcgg 120
aatggccgga acggcggccg gcaacgcctt ggcggcctca ccggcggctt tggcgccttc 180
actcgcccac ttcggcaggt cgtgcgccag gccaaagtag tccttgaatt gggtgaccat 240
gagccgagcg ggcgagaccc atttgccgaa cgtgtccatg gccacgctgg catcaagttc 300
tgccgacccg gtcacaccct gcacaaagtc gccaagcact ccgcccacga tgagcccgct 360
accgtccgag gaccaggtgt gcccggtcaa accgagcgcc ttgccaaggt cggtgagcca 420
aggcggttca ttggtgaaga ttccgctaag cccaaacaac gctttaggaa tgtcggtgag 480
tgcttgcgca tttgcggccc cgctgacagc ttgtccgaca gatgcggcct ggctggccag 540
cccggccggg ttgatggtct gcgccgccgg attgaatggc gacaactgcg tcgccgccgc 600
c 601

<210> SEQ ID NO 99
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 99
tgcgcgatgc cgacgatgcc gcgctgcttg ccgcaatcga ggactgcgcg cgtgccgagg 60
tggccgccgg cgcccgccgc ctgtcagcga tcgccgaact caccagccgg cgcaccggca 120
atgaccagcg ggccgactgg gcgtgcgacg gctgggactg cgcggccgcc gaggtggccg 180
ccgcactgac cgtaagccac cgtaaggcct ccgggcagat gcatctgagc ctcaccctaa 240
accgactgcc ccaggtggcg gcgttgtttt tggccgggca gctcagcgcg cggctggtgt 300
tgatcatcgc ctggcgcacc tacctggttc gcgaccccga agcgctgagt ctgctcgatg 360
ccgccctcgc caaacacgcc acagcgtggg gtccgctgtc ggcccccaaa ctggaaaagg 420
ctatcgactc ctggattgat cggtacgatc ccgccgcact gcgacgcacc cgtatctcgg 480
cccgcagccg cgacctgtgc atcggtgatc ccgacgaaga tgccggcacc gccgcactat 540
ggggccggtt gtttgccacc gacgccgcca tgctggataa gcgcctcacc cagctggccc 600
a 601

<210> SEQ ID NO 100
<211> LENGTH: 601
<212> TYPE: DNA
<213> ORGANISM: Mycobacterium tuberculosis
<220> FEATURE:
<221> NAME/KEY: variation
<222> LOCATION: (301)..(301)
<223> OTHER INFORMATION: SNP

<400> SEQUENCE: 100
atccgctggc tggtggatca ggccccagcg cgggcgcggg cctgctgcgc gcggagtcgc 60
tacctggcgc aggtgggtcg ttgacccgca cgccgctgat gtctcagctg atcgaaaagc 120

```
cggttgcccc ctcggtgatg ccggcggctg ctgccggatc gtcggcgacg ggtggcgccg      180
ctccggtggg tgcgggagcg atgggccagg gtgcgcaatc cggcggctcc accaggccgg      240
gtctggtcgc gccggcaccg ctcgcgcagg agcgtgaaga agacgacgag gacgactggg      300
ccgaagagga cgactggtga gctcccgtaa tgacaacaga cttcccggcc acccgggccg      360
gaagacttgc caacattttg gcgaggaagg taaagagaga aagtagtcca gcatggcaga      420
gatgaagacc gatgccgcta ccctcgcgca ggaggcaggt aatttcgagc ggatctccgg      480
cgacctgaaa acccagatcg accaggtgga gtcgacggca ggttcgttgc agggccagtg      540
gcgcggcgcg gcggggacgg ccgcccaggc cgcggtggtg cgcttccaag aagcagccaa      600
t                                                                     601
```